US010194956B2

United States Patent
Trautwein et al.

(10) Patent No.: US 10,194,956 B2
(45) Date of Patent: Feb. 5, 2019

(54) INTERSPINOUS VERTEBRAL AND LUMBOSACRAL STABILIZATION DEVICES AND METHODS OF USE

(71) Applicant: Paradigm Spine, LLC, New York, NY (US)

(72) Inventors: Frank T. Trautwein, Filderstadt (DE); Gary L. Lowery, Jacksonville, FL (US); Guntmar H. Eisen, Tuttlingen (DE); Rudolf Bertagnoli, Vienna (AT); Marc R. Viscogliosi, New York, NY (US); David I. Biondo, Canton, MI (US)

(73) Assignee: Paradigm Spine, LLC, New York, NY (US)

( * ) Notice: Subject to any disclaimer, the term of this patent is extended or adjusted under 35 U.S.C. 154(b) by 0 days.

(21) Appl. No.: 15/223,972

(22) Filed: Jul. 29, 2016

(65) Prior Publication Data

US 2016/0331417 A1 Nov. 17, 2016

Related U.S. Application Data

(62) Division of application No. 13/926,149, filed on Jun. 25, 2013, now Pat. No. 9,402,657, which is a division
(Continued)

(51) Int. Cl.
*A61B 17/70* (2006.01)
*A61B 17/80* (2006.01)
(Continued)

(52) U.S. Cl.
CPC ...... *A61B 17/7067* (2013.01); *A61B 17/7049* (2013.01); *A61B 17/80* (2013.01);
(Continued)

(58) Field of Classification Search
CPC combination set(s) only.
See application file for complete search history.

(56) References Cited

U.S. PATENT DOCUMENTS 3,648,691 A 3/1972 Lumb et al.
4,554,914 A 11/1985 Kapp et al.
(Continued)

FOREIGN PATENT DOCUMENTS

EP 0322334 6/1989
EP 0649636 4/1995
(Continued)

OTHER PUBLICATIONS

Author Unknown, European Search Report dated Feb. 8, 2010, European Application No. 15184335.6, p. 1-12.
(Continued)

*Primary Examiner* — Sameh Boles
(74) *Attorney, Agent, or Firm* — Tram Nguyen; Farber LLC

(57) ABSTRACT

Implantable devices are provided for stabilizing adjacent vertebrae and the lumbosacral region of a patient. The devices can comprise an interspinous flexible spacer body having a substantially U-shape comprising a superior section, inferior section, and a midsection extending therebetween. The superior and/or inferior sections can include a pair of lateral walls configured to engage a spinous process of a vertebra. Fixation caps can be provided for securing a spinous process of a vertebra to the flexible spacer body. To secure the flexible spacer body between the lumbar vertebra and an adjacent vertebra, an anchor assembly is provided. Also provided are methods of using the implantable devices to stabilize a patient's spine.

5 Claims, 41 Drawing Sheets

Related U.S. Application Data of application No. 11/400,586, filed on Apr. 7, 2006, now Pat. No. 8,470,000.

(60) Provisional application No. 60/669,346, filed on Apr. 8, 2005.

(51) Int. Cl.
*A61B 17/84* (2006.01)
*A61B 17/56* (2006.01)
*A61B 17/68* (2006.01)

(52) U.S. Cl.
CPC ....... *A61B 17/842* (2013.01); *A61B 2017/567* (2013.01); *A61B 2017/681* (2013.01); *A61B 2017/7073* (2013.01)

(56) References Cited

U.S. PATENT DOCUMENTS

| | | |
|---|---|---|
| 4,570,618 A | 2/1986 | Wu |
| 4,573,454 A | 3/1986 | Hoffman |
| 4,604,995 A | 8/1986 | Stephens et al. |
| 4,686,970 A | 8/1987 | Dove et al. |
| 4,773,402 A | 9/1988 | Asher et al. |
| 4,790,297 A | 12/1988 | Luque |
| 4,887,595 A | 12/1989 | Heinig et al. |
| 5,011,484 A | 4/1991 | Breard |
| 5,366,455 A | 11/1994 | Dove et al. |
| 5,375,823 A | 12/1994 | Navas |
| 5,413,576 A | 5/1995 | Rivard |
| 5,415,661 A | 5/1995 | Holmes |
| 5,496,318 A | 3/1996 | Howland et al. |
| 5,540,688 A | 7/1996 | Navas |
| 5,609,634 A | 3/1997 | Voydeville |
| 5,645,599 A * | 7/1997 | Samani ............ A61B 17/7062 606/248 |
| 5,672,175 A | 9/1997 | Martin |
| 5,725,582 A | 3/1998 | Bevan et al. |
| 5,733,284 A | 3/1998 | Martin |
| 5,810,815 A | 9/1998 | Morales |
| 5,836,948 A | 11/1998 | Zucherman et al. |
| 5,860,977 A | 1/1999 | Zucherman et al. |
| 5,868,745 A * | 2/1999 | Alleyne ............ A61B 17/00 128/888 |
| 5,876,404 A | 3/1999 | Zucherman et al. |
| 5,888,223 A | 3/1999 | Bray, Jr. |
| 5,951,553 A | 9/1999 | Betz et al. |
| 5,961,516 A | 10/1999 | Graf |
| 6,048,342 A | 4/2000 | Zucherman et al. |
| 6,068,630 A | 5/2000 | Zucherman et al. |
| 6,074,390 A | 6/2000 | Zucherman et al. |
| 6,090,112 A | 7/2000 | Zucherman et al. |
| 6,149,652 A | 11/2000 | Zucherman et al. |
| 6,152,926 A | 11/2000 | Zucherman et al. |
| 6,156,038 A | 12/2000 | Zucherman et al. |
| 6,183,471 B1 | 2/2001 | Zucherman et al. |
| 6,190,387 B1 | 2/2001 | Zucherman et al. |
| 6,235,030 B1 | 5/2001 | Zucherman et al. |
| 6,238,397 B1 | 5/2001 | Zucherman et al. |
| 6,267,764 B1 | 7/2001 | Zucherman et al. |
| 6,273,914 B1 | 8/2001 | Papas |
| 6,280,444 B1 | 8/2001 | Zucherman et al. |
| 6,312,431 B1 | 11/2001 | Asfora |
| 6,332,882 B1 | 12/2001 | Zucherman et al. |
| 6,332,883 B1 | 12/2001 | Zucherman et al. |
| 6,364,883 B1 | 4/2002 | Santill |
| 6,379,355 B1 | 4/2002 | Zucherman et al. |
| 6,402,750 B1 | 6/2002 | Atkinson et al. |
| 6,419,676 B1 | 7/2002 | Zucherman et al. |
| 6,419,677 B2 | 7/2002 | Zucherman et al. |
| 6,436,099 B1 | 8/2002 | Drewry et al. |
| 6,440,169 B1 | 8/2002 | Elberg et al. |
| 6,451,019 B1 | 9/2002 | Zucherman et al. |
| 6,451,020 B1 | 9/2002 | Zucherman et al. |
| 6,478,796 B2 | 11/2002 | Zucherman et al. |
| 6,500,178 B2 | 12/2002 | Zucherman et al. |
| 6,514,256 B2 | 2/2003 | Zucherman et al. |
| 6,569,164 B1 | 5/2003 | Assaker et al. |
| 6,582,433 B2 | 6/2003 | Yun |
| 6,626,944 B1 | 9/2003 | Taylor |
| 6,652,527 B2 | 11/2003 | Zucherman et al. |
| 6,652,534 B2 | 11/2003 | Zucherman et al. |
| 6,695,842 B2 | 2/2004 | Zucherman et al. |
| 6,699,246 B2 | 3/2004 | Zucherman et al. |
| 6,699,247 B2 | 3/2004 | Zucherman et al. |
| 6,712,819 B2 | 3/2004 | Zucherman et al. |
| 6,733,534 B2 | 5/2004 | Sherman |
| 6,761,720 B1 | 7/2004 | Senegas |
| 6,770,075 B2 | 8/2004 | Howland |
| 6,796,983 B1 | 9/2004 | Zucherman et al. |
| 6,852,128 B2 | 2/2005 | Lange |
| 6,875,212 B2 | 4/2005 | Shaolian et al. |
| 6,899,713 B2 | 5/2005 | Shaolian et al. |
| 6,902,566 B2 | 6/2005 | Zucherman et al. |
| 6,949,123 B2 | 9/2005 | Reiley |
| 7,491,238 B2 | 2/2009 | Arnin et al. |
| 8,128,664 B2 | 3/2012 | Pasquet |
| 2003/0040746 A1* | 2/2003 | Mitchell ............ A61B 17/1606 623/17.11 |
| 2003/0153915 A1 | 8/2003 | Nekozuka et al. |
| 2003/0171749 A1 | 9/2003 | Le Couedic et al. |
| 2003/0191470 A1 | 10/2003 | Ritland |
| 2003/0216736 A1 | 11/2003 | Robinson et al. |
| 2004/0073215 A1 | 4/2004 | Carli |
| 2004/0153071 A1 | 8/2004 | Zucherman et al. |
| 2004/0153072 A1 | 8/2004 | Bonutti |
| 2004/0162617 A1 | 8/2004 | Zucherman et al. |
| 2004/0181282 A1 | 9/2004 | Zucherman et al. |
| 2004/0199255 A1 | 10/2004 | Mathieu et al. |
| 2004/0220568 A1 | 11/2004 | Zucherman et al. |
| 2004/0243239 A1 | 12/2004 | Taylor |
| 2005/0010293 A1 | 1/2005 | Zucherman et al. |
| 2005/0010298 A1 | 1/2005 | Zucherman et al. |
| 2005/0056979 A1 | 3/2005 | Studer et al. |
| 2005/0065514 A1 | 3/2005 | Studer |
| 2005/0075634 A1 | 4/2005 | Zucherman et al. |
| 2005/0101955 A1 | 5/2005 | Zucherman et al. |
| 2005/0113927 A1 | 5/2005 | Malek |
| 2005/0143738 A1 | 6/2005 | Zucherman et al. |
| 2005/0165398 A1 | 7/2005 | Reiley et al. |
| 2005/0196420 A1 | 9/2005 | Zucherman et al. |
| 2005/0203512 A1 | 9/2005 | Hawkins et al. |
| 2005/0203624 A1 | 9/2005 | Serhan et al. |
| 2005/0209603 A1 | 9/2005 | Zucherman et al. |
| 2005/0216017 A1 | 9/2005 | Fielding et al. |
| 2005/0228383 A1 | 10/2005 | Zucherman et al. |
| 2005/0228384 A1 | 10/2005 | Zucherman et al. |
| 2006/0015181 A1* | 1/2006 | Elberg ............... A61B 17/7062 623/16.11 |

FOREIGN PATENT DOCUMENTS

| | | |
|---|---|---|
| EP | 0806212 | 11/1997 |
| EP | 1138268 | 3/2001 |
| EP | 1330987 A1 | 7/2009 |
| FR | 2703239 | 10/1994 |
| FR | 2717675 | 9/1995 |
| WO | 9426192 | 11/1994 |
| WO | 9940866 | 8/1999 |
| WO | 0145576 | 6/2001 |
| WO | 0156489 | 8/2001 |
| WO | 02102259 | 12/2002 |
| WO | 2004024010 | 3/2004 |
| WO | 2004073533 | 9/2004 |
| WO | 2004084743 | 10/2004 |

(56) References Cited

FOREIGN PATENT DOCUMENTS

| | | |
|---|---|---|
| WO | 2005009300 | 2/2005 |
| WO | 2005020860 | 3/2005 |
| WO | 2006106268 | 10/2006 |

OTHER PUBLICATIONS

Author Unknown, Office Action dated May 22, 2012, Japanese Application No. 2008-505598.
Author Unknown, Written Opinion and International Report dated Oct. 18, 2007, International Application No. PCT/US2006/013150.
Author Unknown, Communication (PCT/ISA/206) Relating to Results of Partial International Search dated Aug. 25, 2006, International Application No. PCT/US2006/013150.

\* cited by examiner

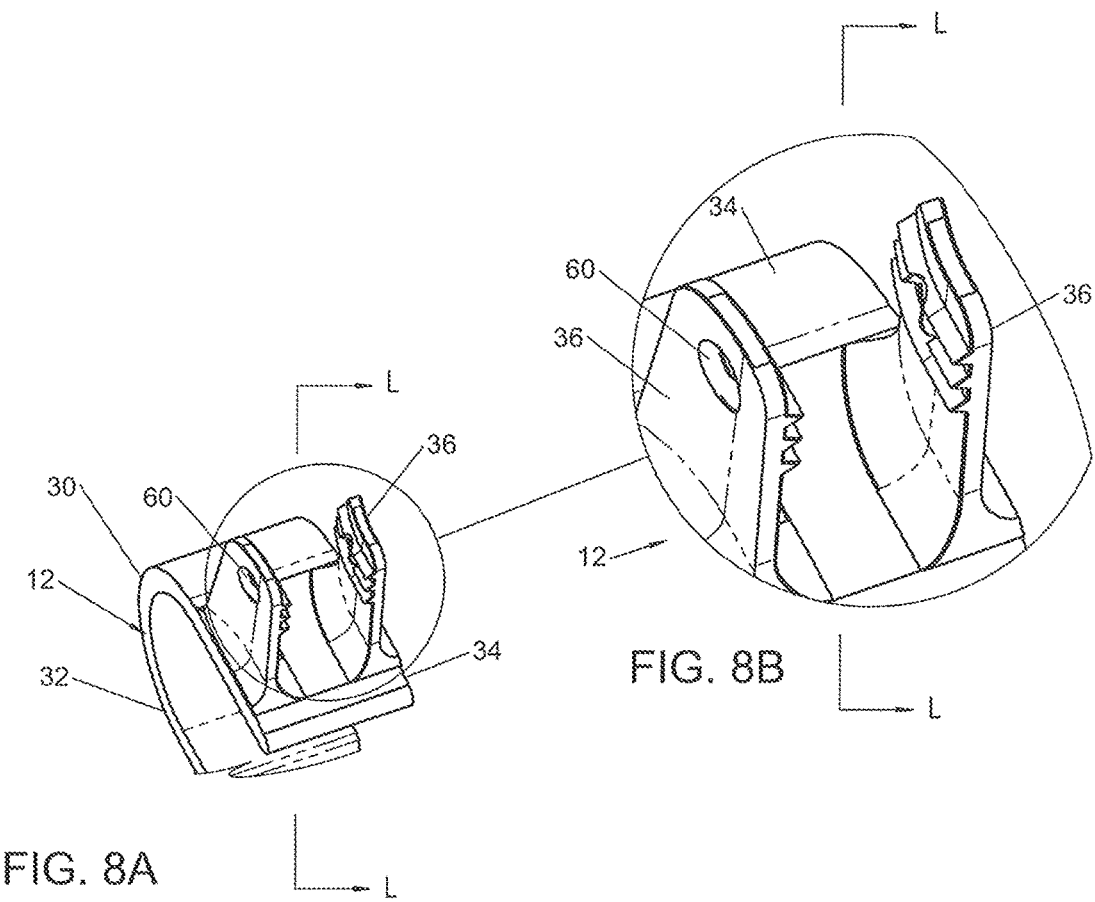

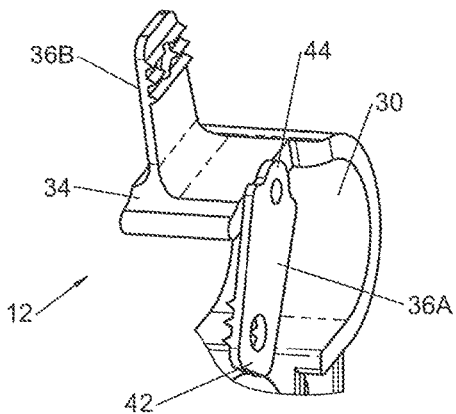
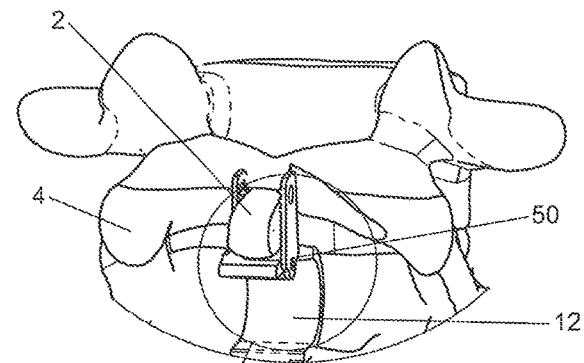
FIG. 13A
FIG. 13B
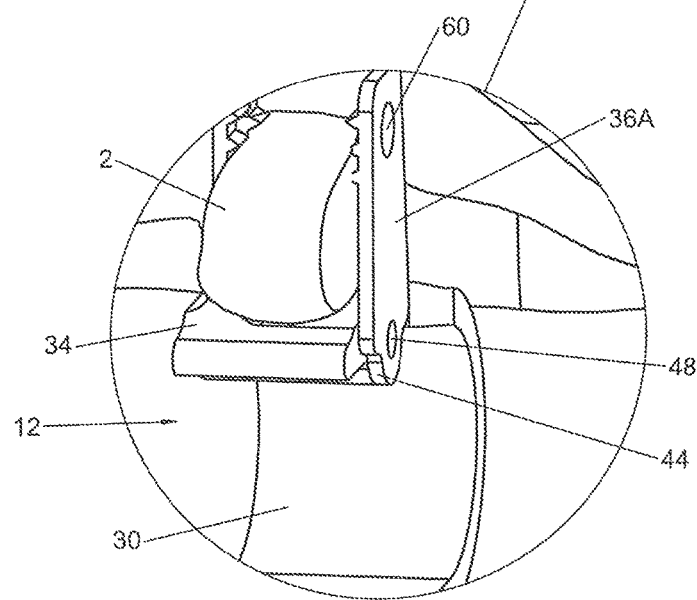
FIG. 13C

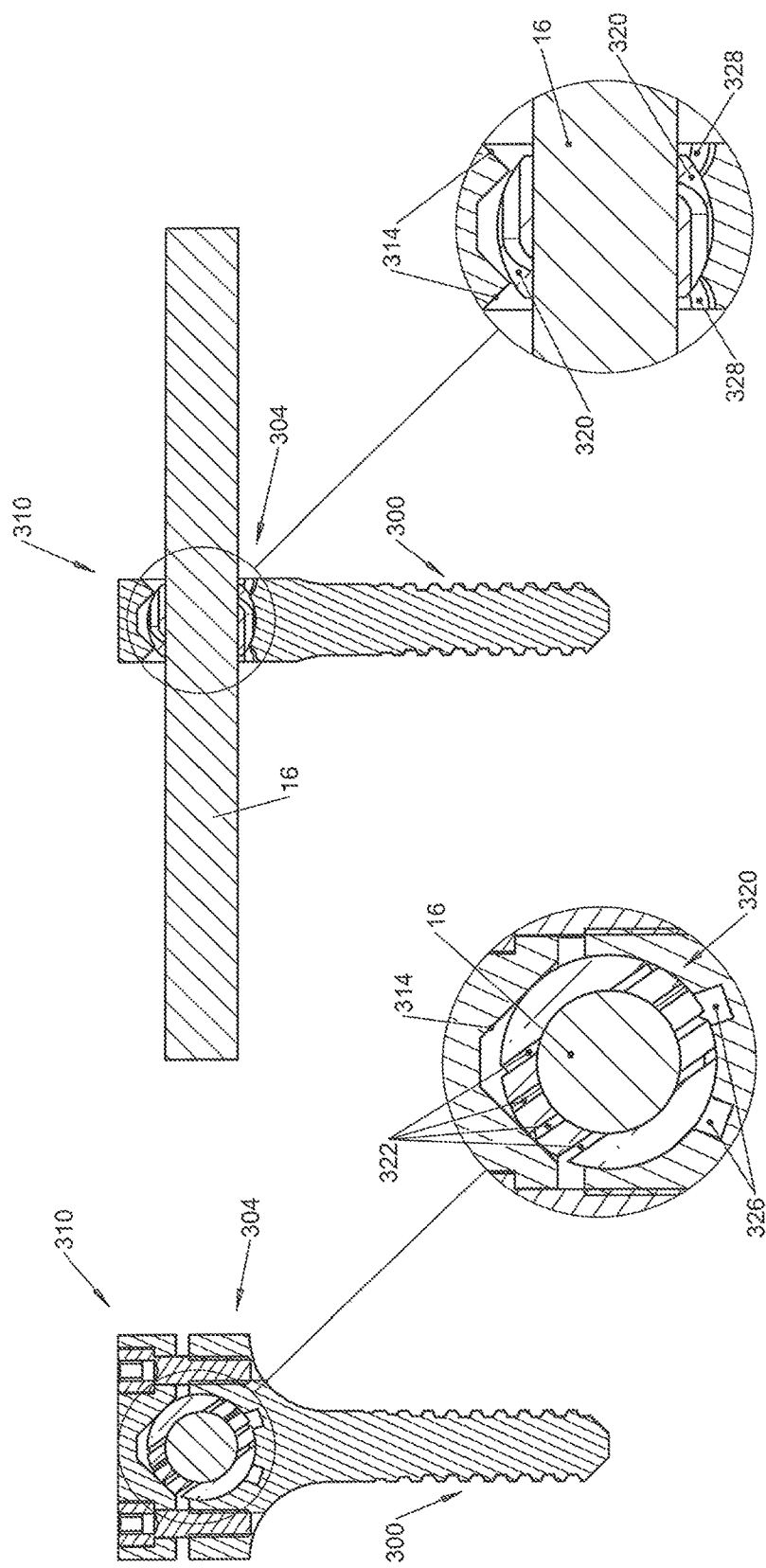

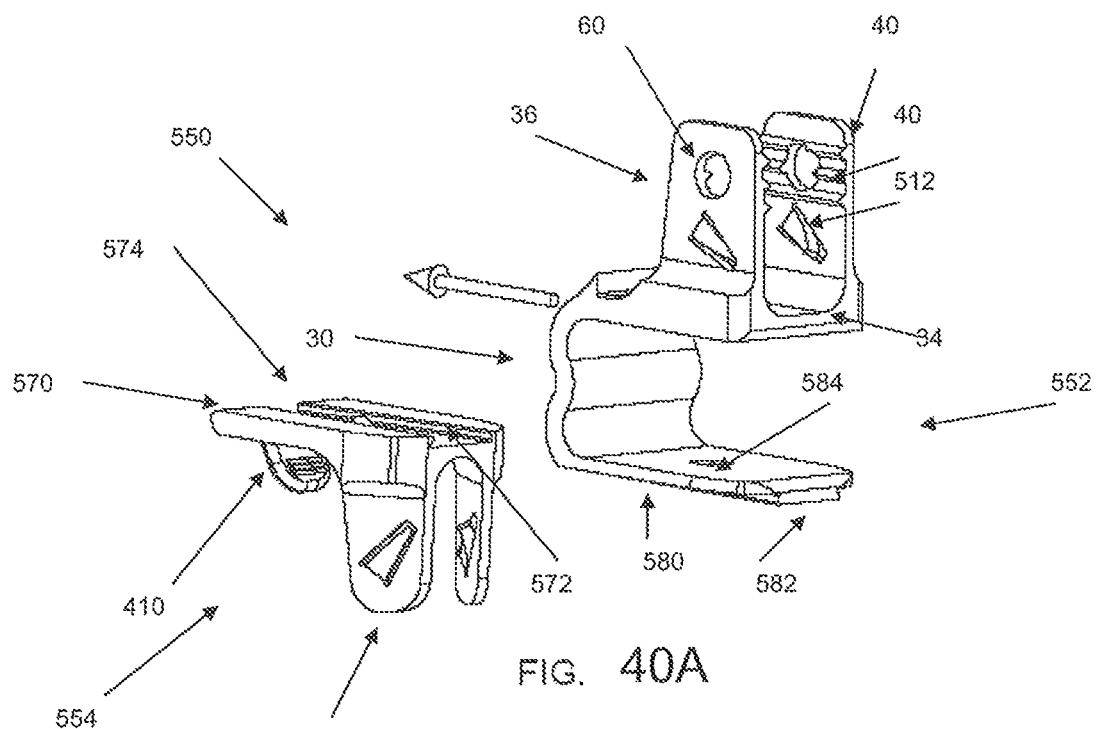
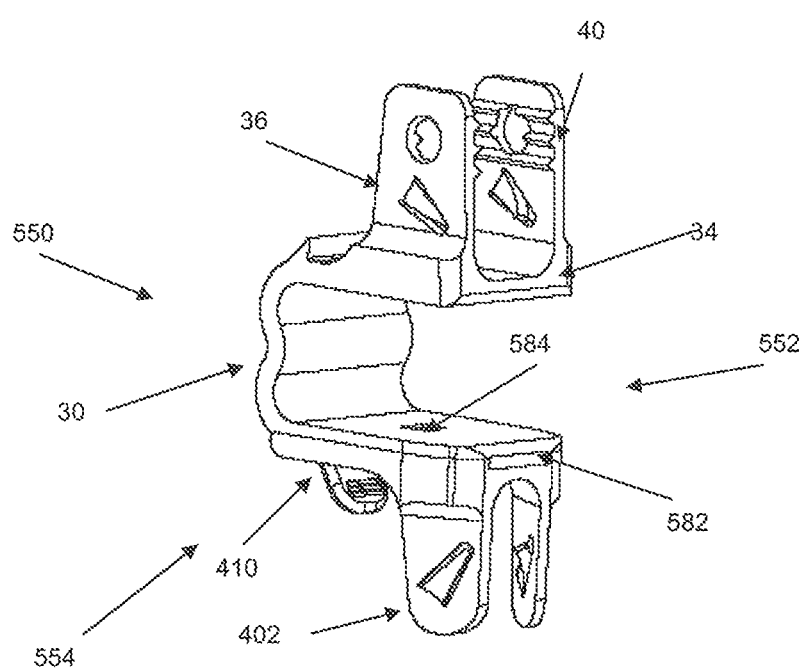
FIG. 40A
FIG. 40B

INTERSPINOUS VERTEBRAL AND LUMBOSACRAL STABILIZATION DEVICES AND METHODS OF USE

CROSS-REFERENCE TO RELATED APPLICATIONS

This a divisional of U.S. patent application Ser. No. 13/926,149, filed Jun. 25, 2013, (now allowed), which is a divisional of U.S. patent application Ser. No. 11/400,586, filed Apr. 7, 2006, now U.S. Pat. No. 8,470,000, which claims benefit of U.S. Provisional Application No. 60/669,346, filed on Apr. 8, 2005, the contents of which are incorporated by reference in their entirety.

FIELD

The present invention relates to devices and methods for treating spinal conditions, and specifically to vertebral stabilization devices and methods of using such devices for stabilizing adjacent vertebrae. More specifically, the present invention relates to interspinous vertebral stabilization devices for placement between the spinous processes of two or more vertebrae and, even more specifically, to lumbosacral stabilization devices for placement between a lumbar vertebra and an adjacent vertebra and methods of using such devices.

BACKGROUND

Diseases of the spine cause significant morbidity. These diseases include abnormalities of the vertebrae, the intervertebral discs, the facet joints, and connective tissue around the spine. These abnormalities can be due to a number of causes, including mechanical injury or degenerative disc disease. Such abnormalities can cause instability to the spine, allowing the vertebral column to become misaligned and producing micromotion between adjacent vertebrae. Vertebral misalignment and micromotion may result in wear to the vertebral bony surfaces and ultimately cause severe pain. Further, these conditions are often chronic and progressive problems.

The treatments for spinal disorders may include long-term medical management or surgery. Medical management is generally directed at controlling the symptoms, such as pain, rather than correcting the underlying problem. For some patients this may require chronic use of pain medications, which may alter patient mental state or cause other negative side effects.

Another treatment option is surgery, which is often highly invasive and may significantly alter the spinal anatomy and function. For example, one surgical treatment for certain spinal conditions includes spinal fusion, whereby two or more vertebrae may be joined using bone grafts and/or synthetic implants. The fusion process is irreversible and may significantly alter vertebral range-of-motion. Further, current surgical procedures are often only applicable to patients in a significantly progressed disease state.

Consequently, spinal surgeons have begun to develop more advanced surgical procedures and spinal stabilization and/or repair devices that are less invasive, may be reversible, and cause a less drastic alteration in the patient's normal anatomy and spinal function. These procedures may be used in an earlier stage of disease progression and, in some situations, may even stop or reverse disease progression.

Recently, a variety of interspinous stabilization devices have become available. These devices may be implanted between the spinous processes of two or more adjacent vertebrae. By stabilizing the spinous processes in this way, significant stress may be taken off the intervertebral discs to prevent disease progression or to improve conditions such as spinal stenosis. In addition, vertebral motion may be controlled without severely altering spinal anatomy.

Current interspinous vertebral implants are configured to be attached to the spinous processes of two or more adjacent vertebrae. Because the sacrum has a very small or non-existent spinous process, these devices cannot be implanted between the fifth lumbar vertebra (L5) and the first sacral vertebra (S1). However, many patients have spinal conditions that affect the L5 and sacral vertebrae. It would therefore be desirable to provide an interspinous vertebral stabilization device which can be implanted between the sacrum and a lumbar vertebra.

SUMMARY OF THE INVENTION

The present invention includes interspinous vertebral and lumbosacral stabilization devices, and methods of using these devices for treating spinal instability conditions. The invention includes interspinous vertebral stabilization devices adapted for placement between the spinous processes of two or more adjacent vertebrae. The invention also includes lumbar stabilization devices adapted to be placed between a lumbar vertebra and an adjacent vertebra, including the first sacral vertebra (S1), to stabilize the lumbosacral region of a patient, and method for using such devices.

One aspect of the invention includes a device for stabilizing a vertebra adjacent or near a sacrum. The device may comprise an implantable, flexible U-shaped spacer body comprising an inferior section, a superior section, a midsection, and a pair of lateral walls extending from the superior section for engaging a spinous process of a lumbar vertebra. The device may also include an anchor assembly for securing the spacer body between a lumbar vertebra and an adjacent vertebra, including the sacrum.

A second aspect of the invention includes an interspinous stabilization device comprising a support rod and a flexible U-shaped spacer body. The spacer body comprises an inferior section, a superior section, and a midsection therebetween. A pair of lateral walls extends from the superior section for engaging a spinous process of a lumbar vertebra. The inferior section may include a base portion configured to couple with the support rod. The device may further comprise at least one fixation element for securing the support rod to an adjacent vertebra.

A third aspect of the invention includes a lumbosacral interspinous stabilization device comprising a flexible, U-shaped spacer body for implantation between a lumbar vertebra and the sacrum. The spacer body comprises an inferior section, a superior section, and a midsection therebetween. A pair of lateral walls extends from the superior section for engaging a spinous process of a lumbar vertebra. The inferior section may include at least one projection that forms a gripping portion for engagement with the sacrum.

A fourth aspect of the invention includes an implantable device for stabilizing an interspinous region of a patient comprising a flexible U-shaped spacer body having an inferior section, a superior section, and a midsection extending therebetween. The device may also provide a fixation cap for engaging the superior section of the spacer body. The cap is configured to secure a spinous process of a vertebra to the spacer body. Also provided is an anchor assembly for securing the spacer body between the vertebra and an adjacent vertebra.

A fifth aspect of the invention includes an interspinous vertebral stabilization device comprising a flexible U-shaped spacer body. The spacer body comprises an inferior section, a superior section, and a midsection therebetween. The spacer body may be configured for placement within the interspinous space of two adjacent vertebrae. The device may also provide a pair of fixation caps, each cap being configured to engage the superior or inferior section of the spacer body. When attached to the spacer body, the caps secure the spinous processes of the two adjacent vertebrae to the spacer body.

A sixth aspect of the invention includes an interspinous vertebral stabilization device comprising a flexible U-shaped spacer body. The spacer body comprises an inferior section including a pair of lateral walls extending therefrom for engaging a spinous process of a vertebra. The spacer body further comprises a superior section including a pair of lateral walls extending therefrom for engaging a spinous process of an adjacent vertebra. A midsection extends between the inferior and superior sections. The spacer body may be configured for placement within the interspinous space of two adjacent vertebrae. The device may also include a pair of fixation caps, each cap being configured for engagement with of the two pairs of lateral walls. When attached to the spacer body, the caps secure the spinous processes of the two adjacent vertebrae to the spacer body.

A seventh aspect of the invention includes an interspinous vertebral stabilization device comprising a flexible U-shaped spacer body. The spacer body comprises an inferior section including a pair of lateral walls extending therefrom for engaging a spinous process of a vertebra. The spacer body further comprises a superior section including a pair of lateral walls extending therefrom for engaging a spinous process of an adjacent vertebra. A midsection extends between the inferior and superior sections. At least one of the lateral walls is selectively movable with respect to another of the lateral walls. The movable lateral wall can be selectively positioned to secure the spinous process of one of the two adjacent vertebrae to the spacer body.

Also provided are methods for stabilizing the lumbosacral region of a patient using the devices of the present invention. Methods for stabilizing the interspinous region of adjacent vertebrae using the devices of the present invention are also provided.

It is to be understood that both the foregoing general description and the following detailed description are exemplary and explanatory only, and are not restrictive of the invention, as claimed.

The accompanying drawings, which are incorporated in and constitute a part of this specification, illustrate several embodiments of the invention and together with the description, serve to explain the principles of the invention.

Additional objects and advantages of the invention will be set forth in part in the description which follows or may be learned by practice of the invention. The objects and advantages of the invention will be realized and attained by means of the elements and combinations particularly pointed out in the appended claims.

BRIEF DESCRIPTION OF THE DRAWINGS

FIG. 8A provides a partial top-down perspective view of a spacer body including curved lateral walls, according to an exemplary disclosed embodiment;

FIG. 8B provides an enlarged view showing details of FIG. 8A;

FIG. 13A provides a partial perspective view of a spacer body having a hinged lateral wall, according to an exemplary disclosed embodiment;

FIGS. 13B and 13C provide partial perspective views of the spacer body of FIG. 13A implanted within a patient;

FIG. 31A provides a cross-sectional view of the polyaxial screw system of FIG. 30 along lines A-A;

FIG. 31B provides a cross-sectional view of the polyaxial screw system of FIG. 30 along lines B-B;

FIG. 31C provides an enlarged view showing details of FIG. 31A;

FIG. 31D provides an enlarged view showing details of FIG. 31B;

FIG. 40A provides an exploded perspective view of a spacer body, according to yet another exemplary disclosed embodiment;

FIG. 40B provides a side perspective view of the spacer body of FIG. 40A assembled.

DESCRIPTION OF THE EMBODIMENTS

The present disclosure provides implantable devices for stabilizing vertebrae when placed between the spinous processes of adjacent vertebrae, and for stabilizing the lumbosacral region of a patient by placement of the device between a lumbar vertebra and an adjacent vertebra, including the first sacral vertebra (S1). As shown in an exemplary embodiment depicted in FIG. 1, the implant or device 10 comprises a spacer body 12 that is configured to be implanted between the spinous process of a lumbar vertebra, such as the fifth lumbar (L5) spinous process, and an adjacent vertebra. An anchor assembly 14 is provided to secure the spacer body 12 to the adjacent vertebra, which can be, for example, the first sacral vertebra (S1).

Figure 1:
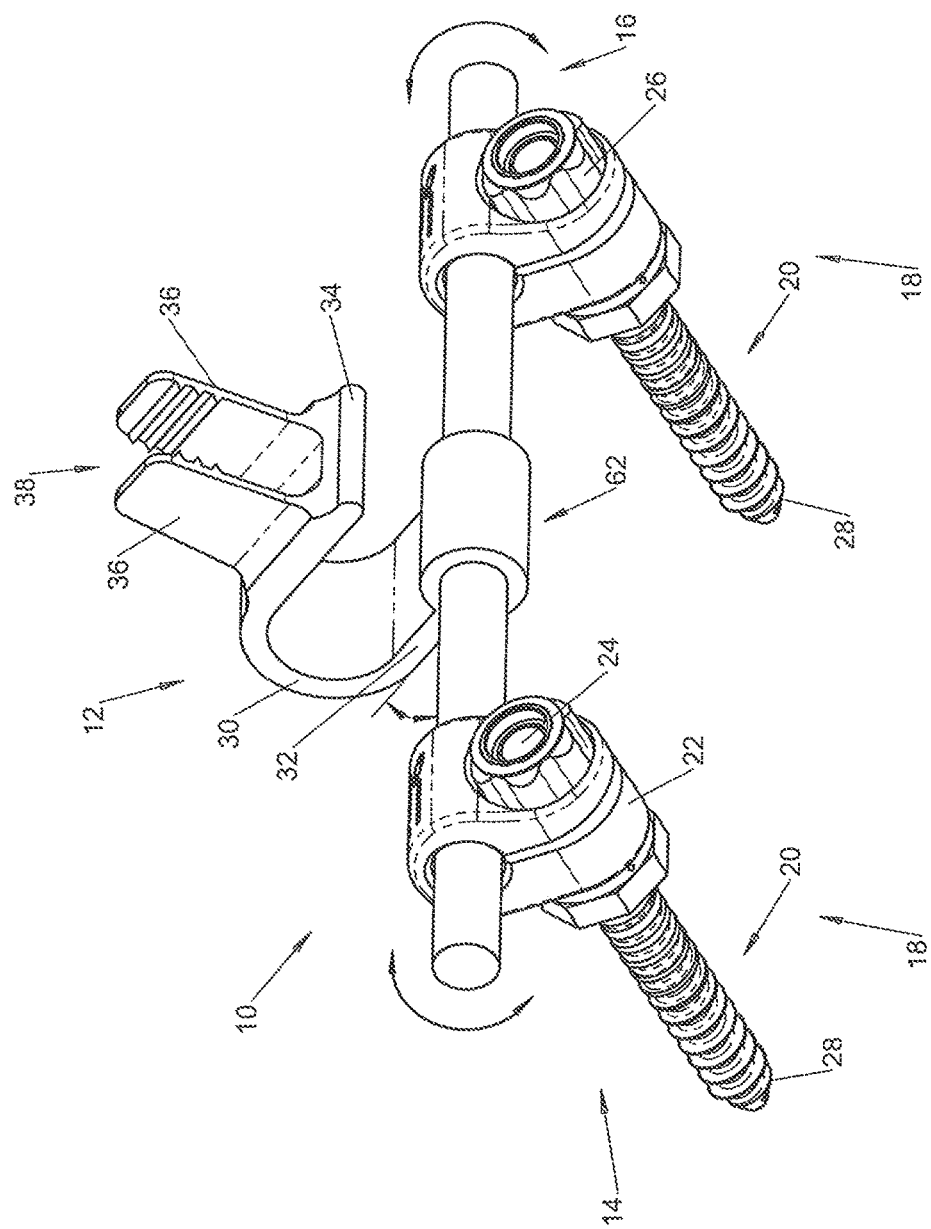
FIG. 1 illustrates an exemplary embodiment of an interspinous lumbosacral stabilization device according to this invention.

The anchor assembly 14 may include a support or a fixation rod 16 to help maintain the spacer body 12 in a proper position with respect to the spine. One or more fixation elements, such as, for example, bone anchors 18 may be used to firmly attach the support or fixation rod 16 onto the patient's sacrum. As illustrated in FIG. 1, the spacer body 12 may be connected to the fixation rod 16 at a base portion 62. Collectively, the spacer body 12, support rod 16, and bone anchors 18 form an interspinous stabilization assembly for stabilizing a lumbar vertebra such as the fifth lumbar vertebra (L5) adjacent the sacrum.

The spacer body 12 may have various shapes, thicknesses, and materials. In one embodiment, the spacer body 12 may include a midsection 30 extending between an inferior section 32 and a superior section 34, as shown in FIG. 1. When implanted in a patient, the superior section 34 is configured to contact a portion of a spinous process, while the inferior section 32 is configured to connect with fixation rod 16. In one embodiment, the midsection 30, inferior section 32, and superior section 34 may together form a substantially U-shaped spacer body 12.

Figure 2A:
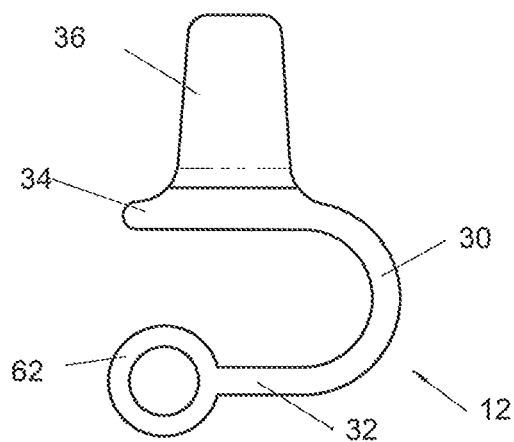
FIGS. 2A-2B provide side views of a spacer body under resting and compressed states, respectively, according to exemplary disclosed embodiments.
Figure 2B:
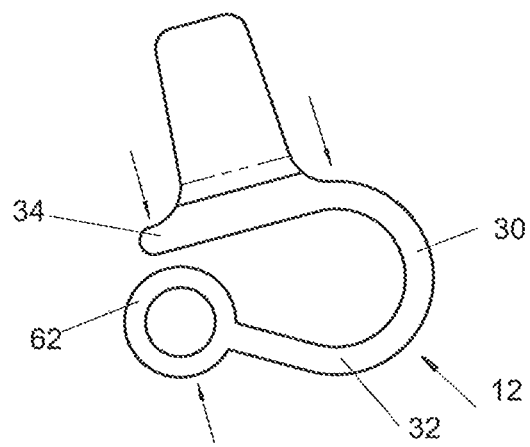

The spacer body 12 may be configured to be flexible and/or bendable, such as, for example, by providing an extendable and/or compressible midsection 30. During spinal extension, a spinous process may exert an inferiorly-directed force on the superior section 34. Likewise, during spinal extension, the fixation rod 16 and/or sacrum may exert a superiorly-directed force on the inferior section 32. As shown in FIGS. 2A and 2B, these forces may cause the superior section 34 and the inferior section 32 to be brought closer together (FIG. 2B) from a resting state in which no external force acts upon the spacer body 12 (FIG. 2A). Compressibility in this way may allow the spacer body 12 to reversibly deform to allow some degree of spinal extension. Thus, the midsection 30 acts as a flexible hinge, allowing the superior section 34 and inferior section 32 to move away from or towards one another.

In addition, the thickness and physical properties of the superior section 34 and/or the inferior section 32 may be selected to allow the superior section 34 and/or the inferior section 32 to bend under ample load. Flexibility (i.e., extendability and/or compressibility) may allow the spacer body 12 to better respond to some normal patient movements. For example, a spacer body 12 having limited compressibility may allow a certain degree of spinal extension, while also controlling spinal flexion, rotation, and/or lateral bending.

The flexibility and/or compressibility of spacer body 12 may be selected based on the body habitus of the patient in whom the device 10 is to be implanted, based on the desired range of motion, and based on various clinical factors. Such clinical factors may include co-morbid conditions, extent of disease, prior surgery, etc. For some patients, a very rigid spacer body 12 may be desirable. For other patients, a more flexible and compressible spacer body 12 may be selected by the surgeon.

The flexibility and/or compressibility of the spacer body 12 may be controlled in a number of ways. For example, the spacer body 12 may be formed from a variety of different materials. In one embodiment, the spacer body 12 may be formed from a single material. Alternatively, the spacer body 12 may include a combination of materials such that the materials forming the midsection 30, inferior section 32, and superior section 34 can differ to provide each of the sections with varying degrees of flexibility and/or compressibility. The specific materials included in each section of the spacer body 12 may be selected based on a desired degree of flexibility and/or compressibility or to provide biocompatibility and/or bioactive characteristics.

A number of biocompatible materials are suitable for forming the spacer body 12 of the present disclosure. For example, in one embodiment, the spacer body 12 may be formed from a medical grade metal such as titanium or titanium alloy. The spacer body 12 may also be formed from, e.g., stainless steel, cobalt chrome, ceramics, and/or polymeric materials, such as ultra-high molecular-weight polyethylene (UHMWPE) and polyetheretherketone (PEEK), either alone or in combination with another one of the suitable materials.

Figure 3A:
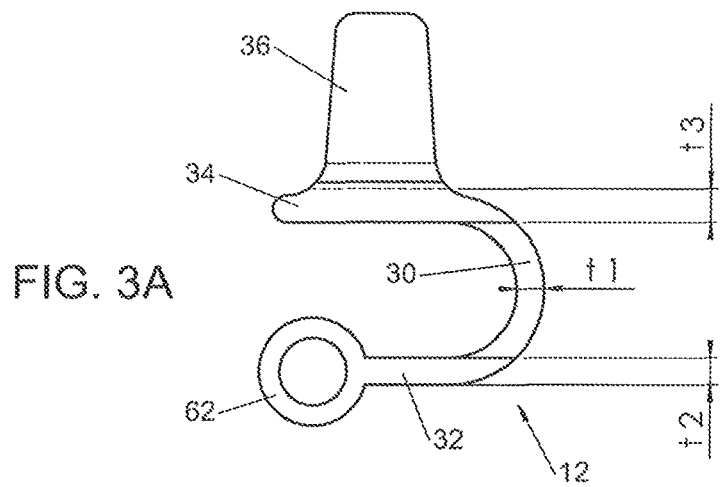
FIGS. 3A-3C provide side views of a spacer body having varying thickness along its length, according to exemplary disclosed embodiments.
Figure 3B:
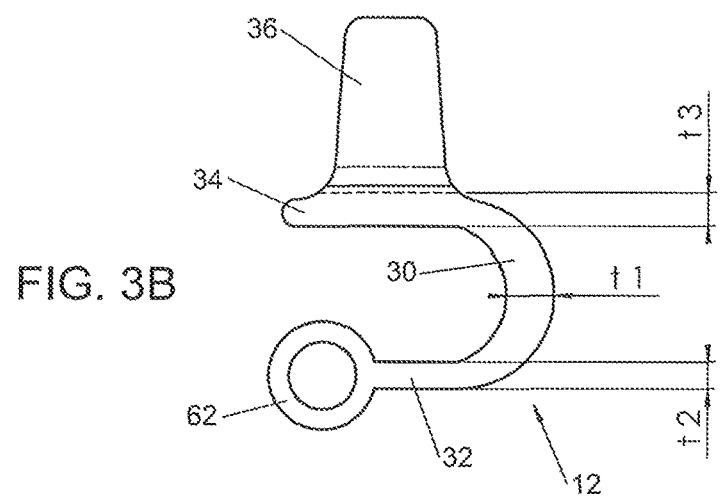
Figure 3C:
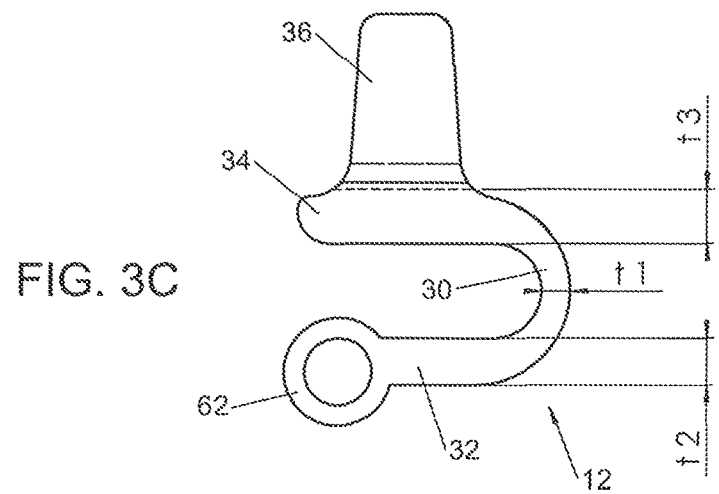

Another way to provide flexibility and/or compressibility to the spacer body 12 is to vary the dimensions of the spacer body 12, such that the degree of flexibility relates to the relative dimensions of the spacer body 12. For example, the spacer body 12 may have a variety of different thicknesses along its length. The thicknesses may be selected to produce a desired degree of flexibility and compressibility. Further, the spacer body 12 may have a variable thickness in one or more different sections. FIGS. 3A-3C illustrate a variety of thickness configurations for the spacer body 12, in which the midsection 30 has a thickness $t_1$, the inferior section 32 has a thickness $t_2$ and the superior section 34 has a thickness $t_3$. In one embodiment, thickness $t_1$, thickness $t_2$, and thickness $t_3$ may be approximately equal (FIG. 3A). In another embodiment, thickness $t_1$ may be greater than thicknesses $t_2$ and $t_3$ (FIG. 3B), and in still another embodiment, thickness $t_1$ may be less than thicknesses $t_2$ and $t_3$ (FIG. 3C). Hence, as shown in FIGS. 3B and 3C, the thickness and consequently the flexibility of the spacer body 12 can vary along its length.

Figure 4A:
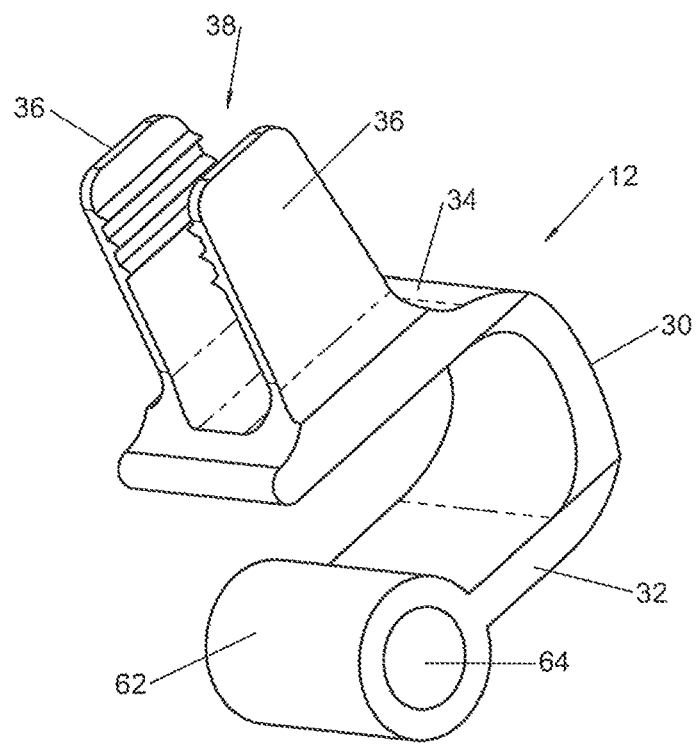
FIG. 4A provides a perspective view of a spacer body having a variable width along its length, according to another exemplary disclosed embodiment.
Figure 4B:
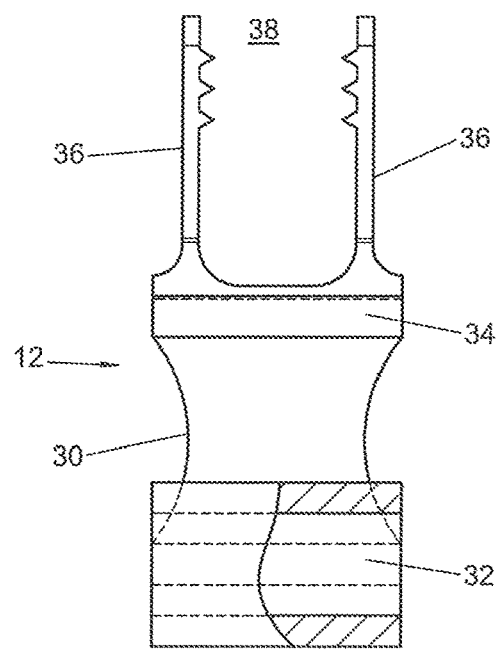
FIG. 4B provides a rear view of the spacer body of FIG. 4A.

Yet another way to affect the flexibility of the spacer body 12 is to vary the width of the body 12 along its length. For instance, as illustrated in FIG. 4A, the spacer body 12 can have a width at the midsection 30 that is less than the width of either the inferior section 32 or superior section 34. Such a configuration would provide the spacer body 12 with an hourglass-like configuration, when viewed from the rear as shown in FIG. 4B.

To limit the compression of the midsection 30 of the spacer body 12, it is contemplated that a bearing cushion (not shown) can be placed between the superior 34 and inferior sections 32 within the spacer body 12. The bearing cushion can be similar to the one described in U.S. Pat. No. 5,645,599 to Samani, the contents of which are hereby incorporated in its entirety by reference. The bearing cushion makes it possible to limit the closing together of the two sections 32, 34 and to ensure a supplementary cushioning of the vertebra 4 if such is desired. The cushion can be made of a suitable elastic material, either woven material or synthetic material, and can be fixed to the sections 32, 34 by any suitable means, such as for example by adhesive bonding.

Figure 5:
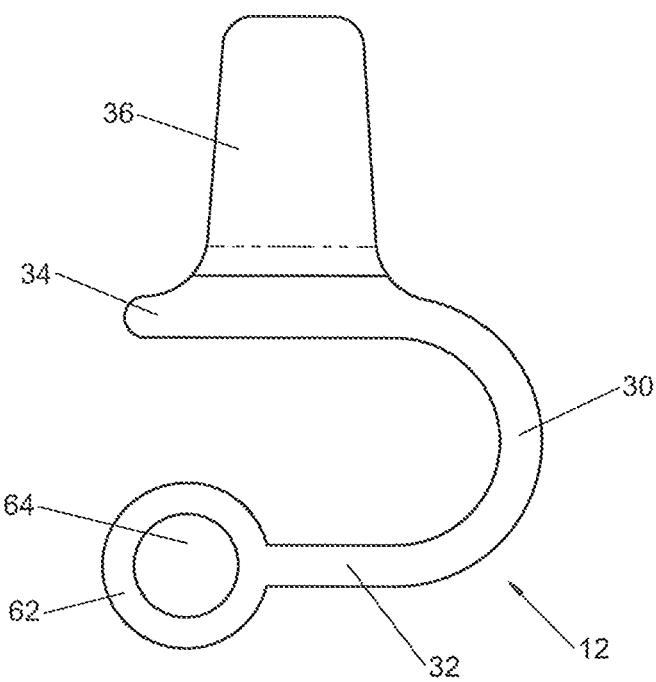
FIG. 5 provides a side view of a spacer body, according to an exemplary disclosed embodiment.

To engage the spinous process of a vertebra, the spacer body 12 may be provided with a pair of lateral walls or brackets 36 that extend from the superior section 34, as shown in FIG. 5. The pair of lateral walls 36 define a stirrup 38 for receiving a spinous process. In one embodiment, the lateral walls or brackets 36 may be configured to engage the spinous process of a lumbar vertebra near the sacrum and secure the spacer body 12 to the spinous process. For example, the brackets 36 may be configured to engage the spinous process of the fifth lumbar vertebra (L5) adjacent the sacrum.

Figure 6A:
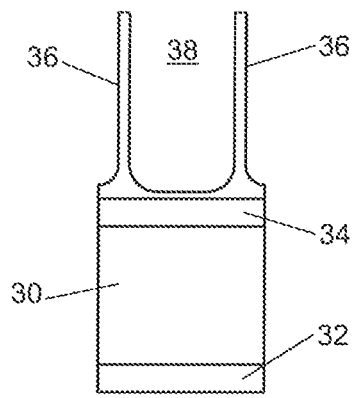
FIGS. 6A-6C provide rear views of a spacer body, according to exemplary disclosed embodiments.
Figure 6B:
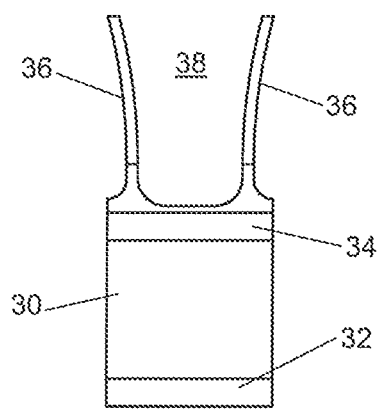
Figure 6C:
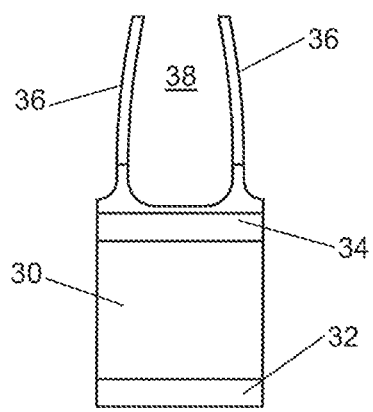

The lateral walls 36 may have a number of orientations with respect to the spacer body 12. For example, as shown in FIGS. 6A-6C, lateral walls 36 may extend in a variety of angles with respect to the superior section 34. In one embodiment, the lateral walls 36 may form a 90 degree angle with respect to the superior section 34 (FIG. 6A). In other embodiments, the lateral walls 36 may form an obtuse angle (FIG. 6B) or an acute angle (FIG. 6C) with respect to the superior section 34. In addition, spacer bodies 12 can be provided with lateral walls 36 of various sizes or heights to accommodate a variety of different interspinous spaces between vertebrae. Likewise, the lateral walls 36 of different spacer bodies 12 may be provided at different locations along the length of the superior sections 34, in order to provide a greater variety of sizes and shapes. The surgeon can thus select a suitably shaped and sized spacer body 12 depending on the particular vertebra to be supported and the natural anatomy of the patient.

Further, the lateral walls 36 may also be adjustable with respect to the spacer body 12. For example, in one embodiment, the lateral walls 36 may form an obtuse angle with respect to the superior section 34 before implantation. The lateral walls 36 may be formed of a malleable material such that, after implantation, the surgeon may compress the lateral walls 36 together to reduce the gap between the lateral walls 36, thereby securely fixing the spacer body 12 to the spinous process of the vertebra. The compression may be accomplished, for example, by pinching or squeezing the lateral walls 36 towards one another using surgical pliers or forceps.

Figure 7A:
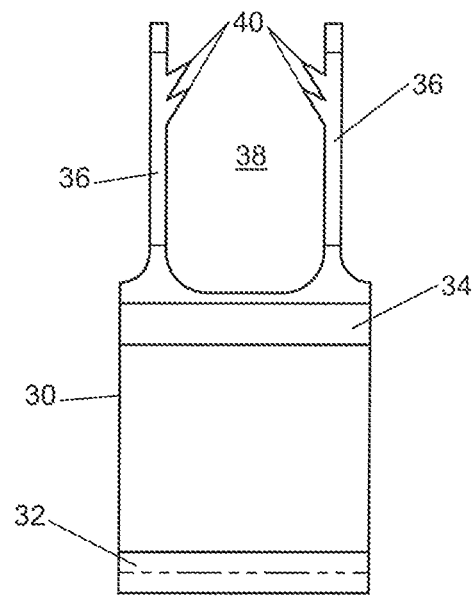
FIG. 7A provides a rear view of a spacer body including barbs, according to an exemplary disclosed embodiment.
Figure 7B:
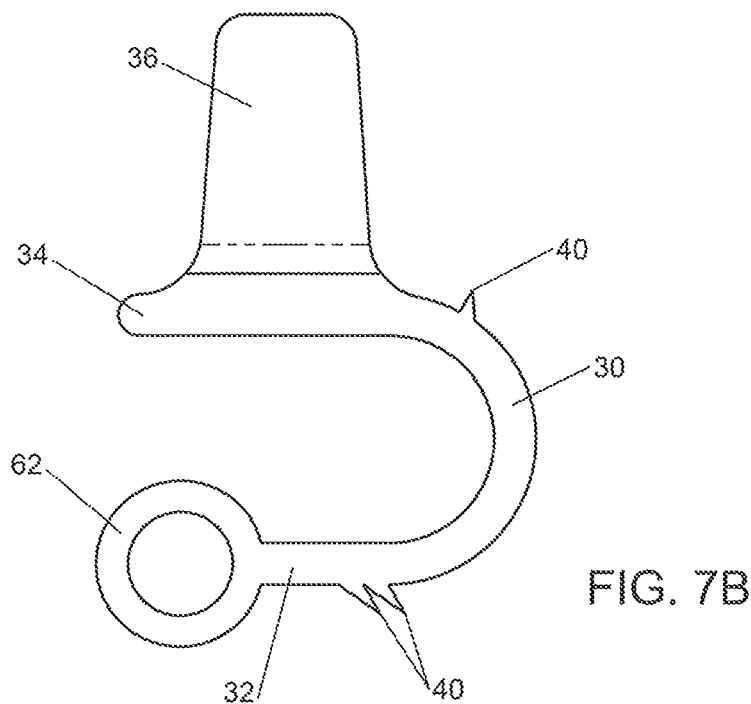
FIG. 7B provides a side view of a spacer body including barbs, according to an exemplary disclosed embodiment.

To further enhance the ability of the device 10 to be secured to the surrounding bone and soft tissue once implanted, the device 10 may include a number of surface modifications. For example, sections of the spacer body 12, lateral walls 36, anchors 18, and/or fixation rod 16 may include surface alterations that may facilitate tissue attachment, bonding or fixation. These alterations may include surface teeth, barbs, beads, surface roughening, or the addition of bioactive agents to one or more sections of the device 10. For example, the device 10 may include one or more barbs 40 for securing the device 10 to bone and/or soft tissue. As shown in FIGS. 7A and 7B, barbs 40 may be located on the spacer body 12, such as on an outer surface of the midsection 30, inferior section 32 and/or superior section 34 (FIG. 7B). Alternatively, or in addition, the barbs 40 may be located on an inner surface of the lateral walls 36 (FIG. 7A). The barbs 40 may help the spacer body 12 securely engage connective tissue or a bony surface of a vertebra, such as the spinous process of the vertebra.

Further, the device 10 may also include roughened or porous surfaces. The roughened or porous surfaces may enhance attachment between implant surfaces and bone tissue. In addition, some porous surfaces may facilitate tissue ingrowth to form a biological bond between sections of the device 10 and the surrounding bone and/or soft tissue. Roughened or porous surfaces may be included on any portion of the device 10, including the spacer body 12, anchors 18, lateral walls 36, and/or fixation rod 16.

The surface of the device 10 may also include biologically active agents. These agents may include osteogenic factors to further facilitate bonding between components of the device 10 and the surrounding bone and/or soft tissue. Further, the device 10 may include therapeutic agents such as antibiotics, steroids, anti-thrombotic agents, anti-inflammatory drugs, and/or analgesic agents. In one embodiment, the biologically active agent may be contained in a coating on the device. Alternatively, or in addition, the device may be porous and the biologically active agent may be contained in the pores of the device. The biologically active agent may be, for example, bone morphogenic protein (BMP) for inducing cartilage or bone growth.

Figure 9A:
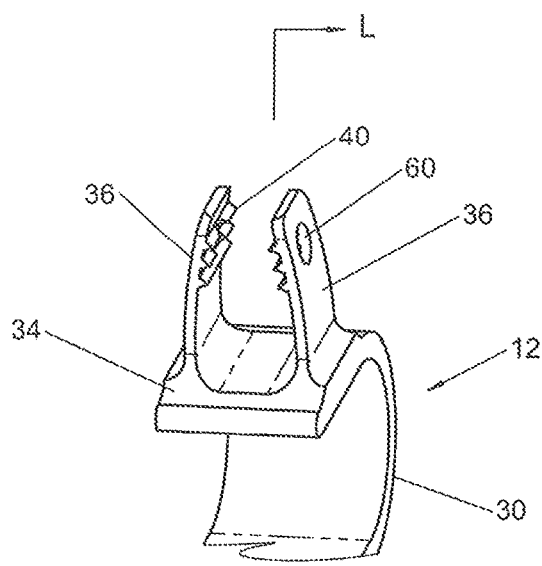
FIG. 9A provides a partial perspective view of a spacer body including curved lateral walls, according to an exemplary disclosed embodiment.
Figure 9B:
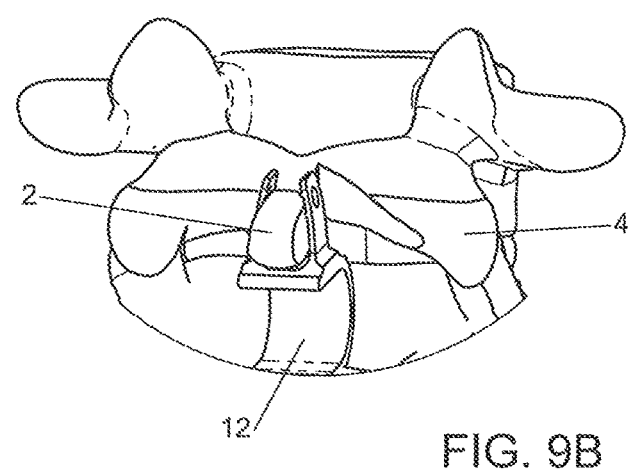
FIG. 9B provides a partial perspective view of the spacer body of FIG. 9A implanted within a patient.

To further enhance the fixation of the spinous process within the stirrup 38 defined by the lateral walls 36 of the spacer body 12, the lateral walls 36 may be curved or angled with respect to the longitudinal axis L of the spacer body 12. For example, FIGS. 8A and 8B show lateral walls 36 that curve away from the longitudinal axis L of the spacer body 12 along the length of the lateral walls 36. The lateral walls or brackets 36 can also be bent or curved inwards or outwards along their length with respect to the longitudinal axis L of the spacer body 12 to accommodate the patient's natural anatomical curves of the laminae. FIG. 9A illustrates a spacer body 12 having lateral walls 36 that bend inward with respect to the longitudinal axis L of the spacer body 12. Such curved brackets 36 allow even greater conformity around the spinous process 2, and therefore better fixation of the device 10 to the vertebra 4, as shown in FIG. 9B.

Figure 10A:
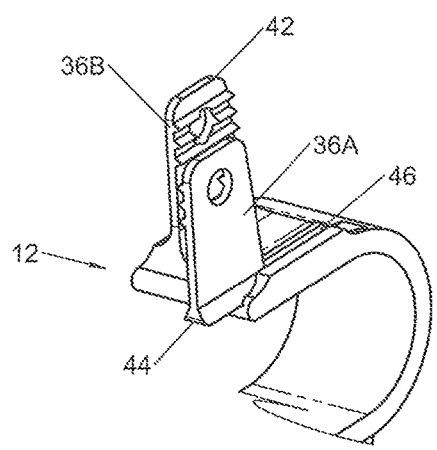
FIG. 10A provides a partial perspective view of a spacer body having a detachable lateral wall, according to an exemplary disclosed embodiment.
Figure 10B:
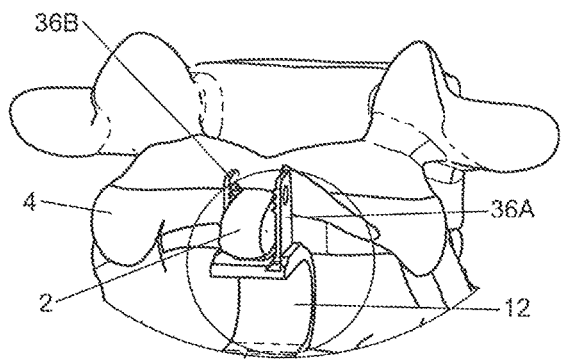
FIGS. 10B and 10C provide partial perspective views of the spacer body of FIG. 10A implanted within a patient.
Figure 10C:
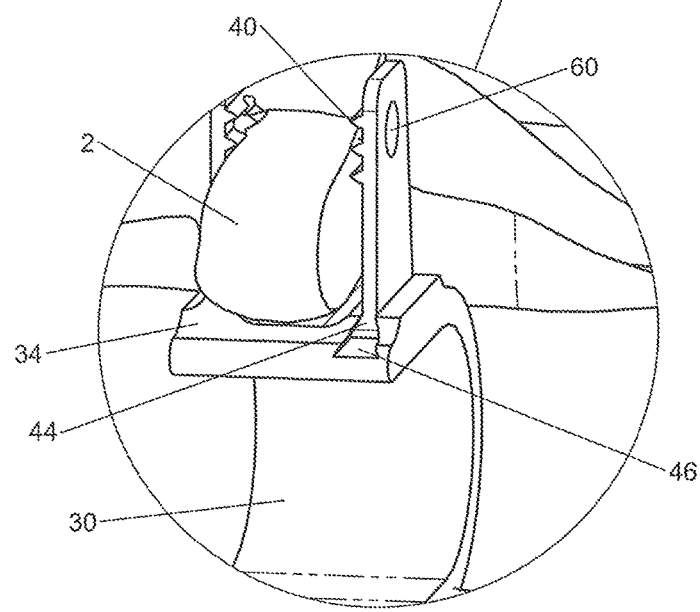

In another exemplary embodiment, at least one of the lateral walls or brackets 36 may be removably attachable to the spacer body 12. For example, as shown in FIGS. 10A-10C, one of the pair of lateral walls or brackets 36A can be formed as an attachable element to the spacer body 12, while the other lateral wall or bracket 36B is permanently affixed or integral with the spacer body 12. The attachable bracket 36B can include a first free end 42 and an opposed, second attachment end 44 that is shaped to complement a slot or groove 46 on the superior section 34, thereby forming a secure connection with the spacer body 12.

Figure 11A:
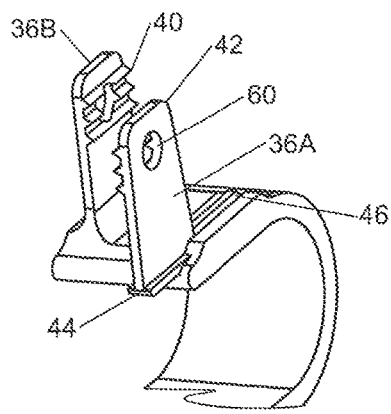
FIG. 11A provides a partial perspective view of a spacer body having a detachable lateral wall, according to an exemplary disclosed embodiment.
Figure 11B:
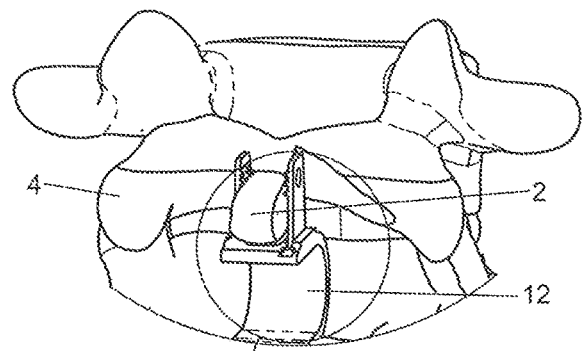
FIGS. 11B and 11C provide partial perspective views of the spacer body of FIG. 11A implanted within a patient.
Figure 11C:
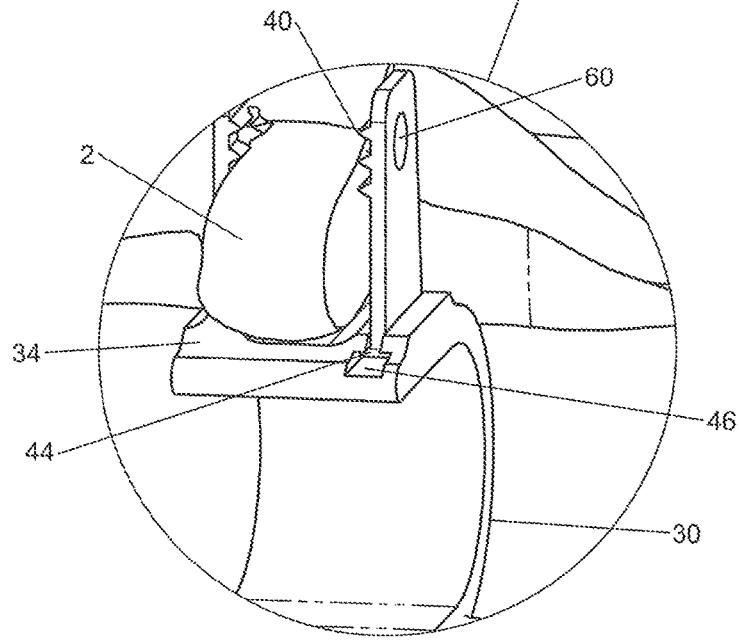
Figure 12A:
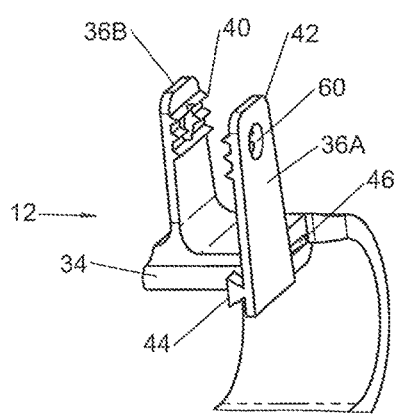
FIG. 12A provides a partial perspective view of a spacer body having a detachable lateral wall, according to an exemplary disclosed embodiment.
Figure 12B:
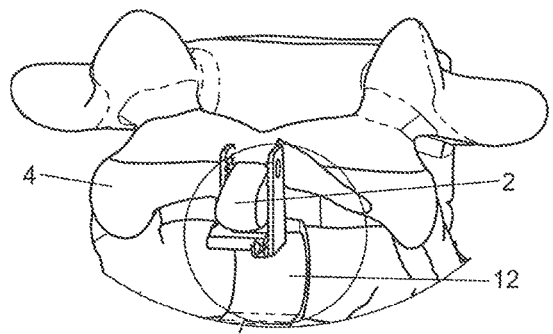
FIGS. 12B and 12C provide partial perspective views of the spacer body of FIG. 12A implanted within a patient.
Figure 12C:
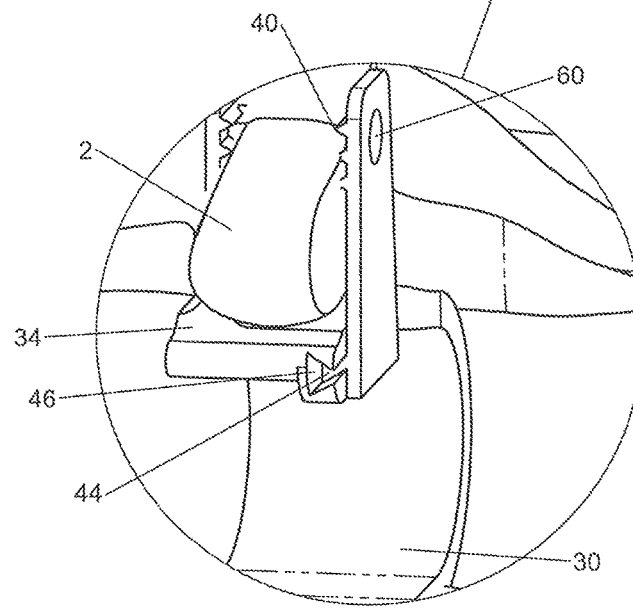

As shown in FIGS. 10A-10C, the attachment end 44 can be formed as a flared end or dovetail for sliding engagement with a dovetail groove 46 on the superior section 34 once the spacer body 12 has been implanted in position. FIGS. 11A-11C show an attachable bracket 36A having an attachment end 44 shaped as a "T" for sliding engagement with a T-shaped groove 46 on the superior section 34 of the spacer body 12. Further, instead of slidably attaching to a groove 46 on a top surface of the superior section 34 of the spacer body, the attachable bracket 36A can slide onto a groove 46 which is formed on a side surface of the superior section 34. For example, as shown in FIGS. 12A-12C, the attachment end 44 of bracket 36A is configured as a dovetail to slidingly engage a dovetail groove 46 on a side surface of superior section 34 of spacer body 12. Although attachment end 44 has been described hereinabove as having a dovetail or T-shaped configuration, it is understood that the attachment end 44 can include other shapes known to one skilled in the art for forming a secure attachment to a complementarily shaped groove 46 on the superior section 34.

In yet another exemplary embodiment, instead of having a freely detachable bracket 36A the spacer body 12 can include a movable, pivotable bracket 36A which can be hinged to the superior section 34. For example, as shown in FIGS. 13A-13C, the second, attachment end 46 of bracket 36A can include an aperture 48 for placement of a pin 50 therethrough to pivotably secure the bracket 36A to a side surface of superior section 34. In this embodiment, the pivotable bracket 36A can be folded down (FIG. 13A) prior to implantation and then after the spacer body 12 has been placed in its correct position, the pivotable bracket 36A can be folded up to rest against and engage the spinous process 2 of the vertebra 4, as shown in FIGS. 13B and 13C.

Figure 14A:
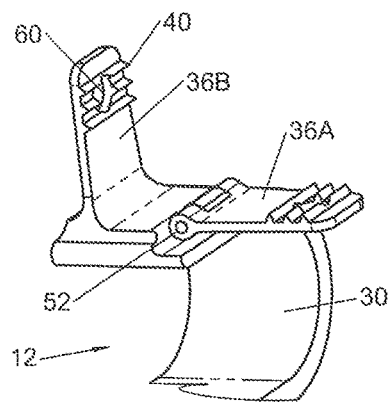
FIG. 14A provides a partial exploded view of a spacer body having a foldable lateral wall, according to an exemplary disclosed embodiment.

In still a further exemplary embodiment, the movable, adjustable bracket 36A can be hinged to the superior section 34 of the spacer body, as shown in FIG. 14A. In this embodiment, the movable bracket 36A can be attached to the spacer body 12 by a hinge joint 52 that allows the bracket 36A to fold up and down. This foldability allows the bracket 36A to move between a position in which the movable bracket 36A is substantially perpendicular to the respective adjacent bracket 36B (FIG. 14A), and a position in which the movable bracket 36A is substantially parallel to the adjacent bracket 36B (FIGS. 14B and 14C) to engage the spinous process 2.

Figure 14B:
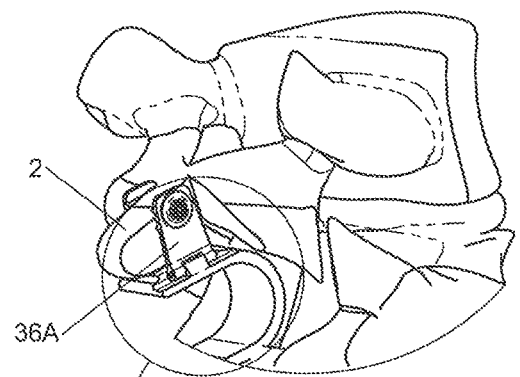
FIGS. 14B and 14C provide partial perspective views of the spacer body of FIG. 14A implanted within a patient.
Figure 14C:
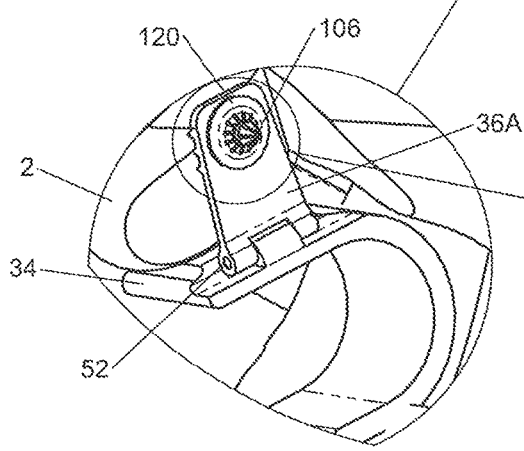
Figure 14D:
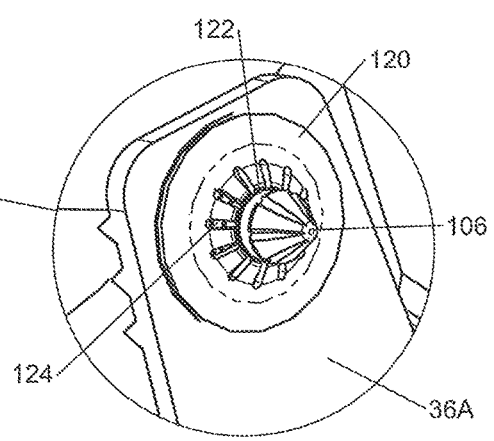
FIG. 14D provides an enlarged view showing details of FIG. 14C.
Figure 15:
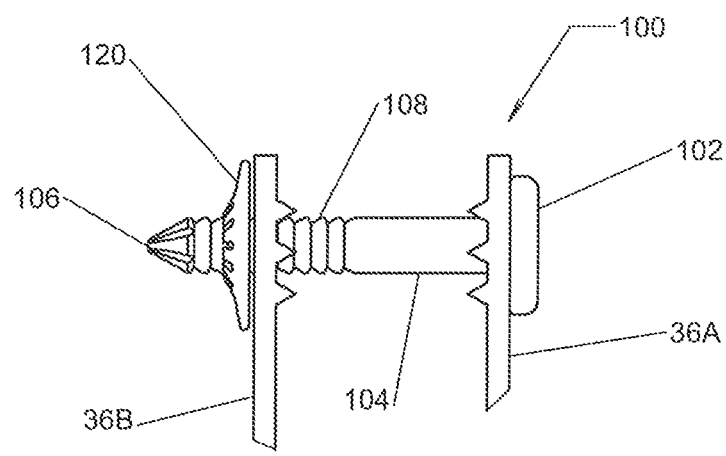
FIG. 15 provides a side view of a bone fastener, according to an exemplary disclosed embodiment.

The lateral walls or brackets 36 of the present invention can also include an aperture 60 for receiving a bone screw, fastener or rivet to fix the brackets 36 to the spinous process 2. Such fastening members would ensure that the brackets 36 are laid flat against the spinous process 2 in order to avoid any play of the process with respect to the brackets 36. For example, as shown in FIGS. 14B-14C, each of the brackets 36A, 36B can be provided with an aperture 60 configured to receive a rivet or fastener 100, shown in greater detail in FIG. 15. The rivet 100 can include a cap 102, an elongate body 104 extending from the cap 102, the elongate body 104 including a plurality of teeth 108 and terminating at a tapered distal end 106. The elongate body 104 is configured to extend between the apertures 60 of the brackets 36A, 36B. A washer 120 can be provided to maintain the rivet 100 within the apertures 60. As shown in FIG. 14C and in greater detail in FIG. 14D, the washer 120 includes an aperture 122 for receiving the tapered distal end 106 of the rivet 100. Slots 124 around the aperture 122 enable the washer 120 to flex so that the tapered distal end 106 can be pushed through the aperture 122 and the washer 120 to close around the teeth 108 of the rivet 100.

Figures 16A, 16B:
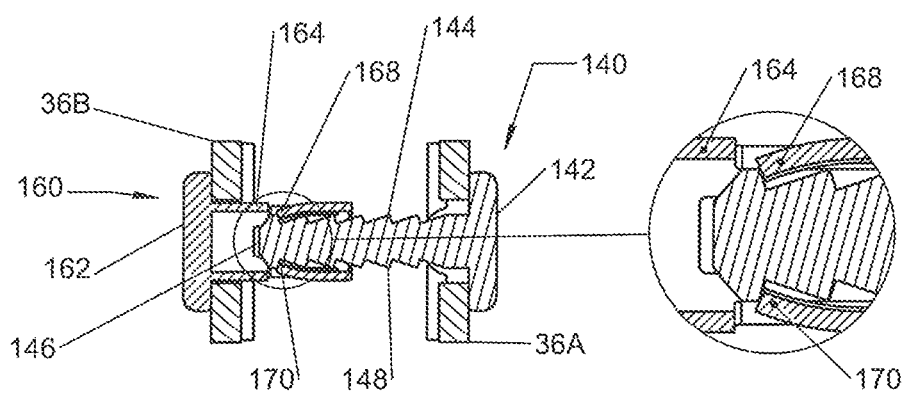
FIG. 16A provides a cross-sectional view of the bone fastener of FIG. 16C, according to an exemplary disclosed embodiment.
FIG. 16B provides an enlarged view showing details of FIG. 16A.
Figures 16C, 16D:
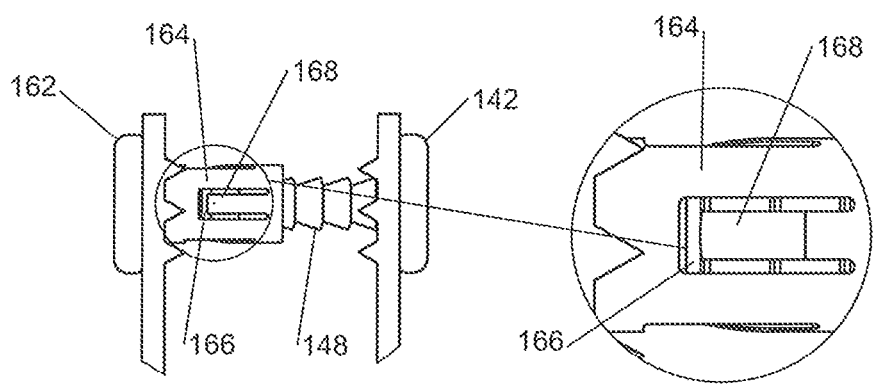
FIG. 16C provides a side view of the bone fastener of FIG. 16A.
FIG. 16D provides an enlarged view showing details of FIG. 16C.

FIGS. 16A-16D illustrate another exemplary embodiment of a bone fastener or pin 140 suitable for use with the brackets 36 of the present invention. Fastener 140 includes a head 142, an elongate body 144 having teeth 148 extending thereabout to a distal end 146. To secure the fastener 140 between the apertures 60, a cap 160 is provided which has a head 162 and a body 164 extending therefrom for receiving the distal end 146 of the fastener 140. As shown in greater detail in FIG. 16D, the hollow body 164 can include one or more U-shaped slots 166, with each slot 166 defining a finger projection 168 therein. Each of the finger projections 168 has a curved end portion 170 bent towards the central axis of the hollow body 164 for engaging the teeth 148 of the fastener 140, as illustrated in FIG. 16A and in greater detail in FIG. 16B. In one exemplary embodiment, the cap 160 includes two pairs of finger projections 168, with each pair being diametrically opposed. The pairs of finger projections 168 can be staggered with respect to the longitudinal axis A-A of the cap 160, thereby providing a more controlled level of attachment by providing two distinct areas within the slotted cavity 166 for capturing the teeth 148 of the fastener 140. In use, the cap 160 is placed through the aperture 60 of the bracket 36 and then pushed towards the fastener 140 in a ratchet-like fashion until the heads 142, 162 of the fastener 140 and cap 160 are flush with the outer surface of the brackets 36, locking together the fastener 140 and cap 160 and thereby also providing an overall smooth outer surface that prevents trauma or injury to the nearby soft or bony tissue.

Figure 17A:
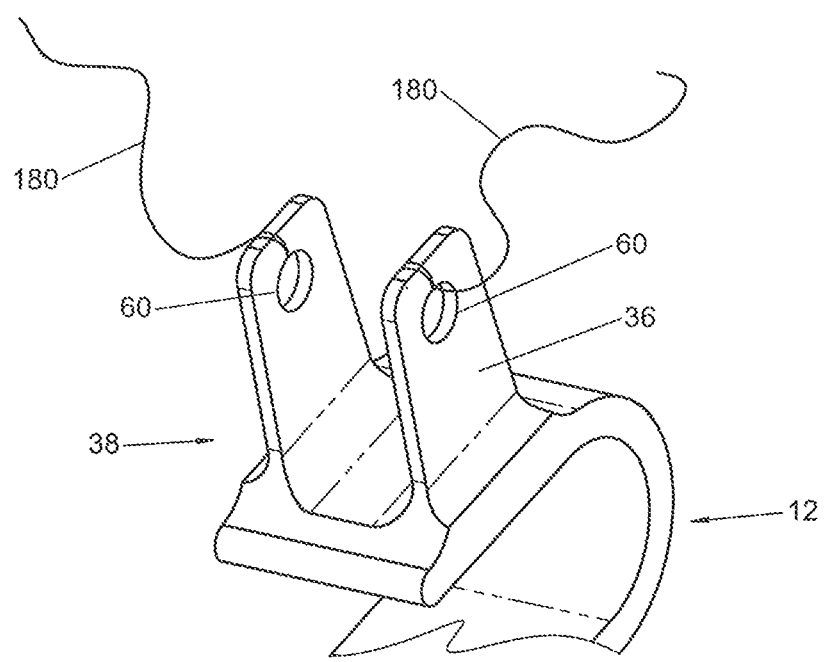
FIG. 17A provides a perspective view of a spacer body and flexible fixation member, according to an exemplary disclosed embodiment.

It is also contemplated that the brackets 36 of the spacer body 12 may be used with one or more flexible fixation elements to further secure the device 10 to one or more spinous processes. In one embodiment shown in FIG. 17A, the lateral walls or brackets 36 of flexible spacer body 12 may include one or more apertures 60 for attaching a flexible fixation element 180. The flexible fixation element 180 may include synthetic or natural materials. For example, the flexible fixation element 180 may include any type of synthetic or natural suture material. The flexible fixation element 180 may also include grafts of ligaments, tendon, fascia, or muscle, and the grafts may include autografts, allografts, or xenografts having sufficient strength and pliability to tie around a spinous process of a vertebra, such as for example, a lumbar vertebra. Alternatively, the flexible fixation element may be a woven fabric, mesh, or webbing such as a cable-binder type strap for placement around the spinous process.

Figure 17B:
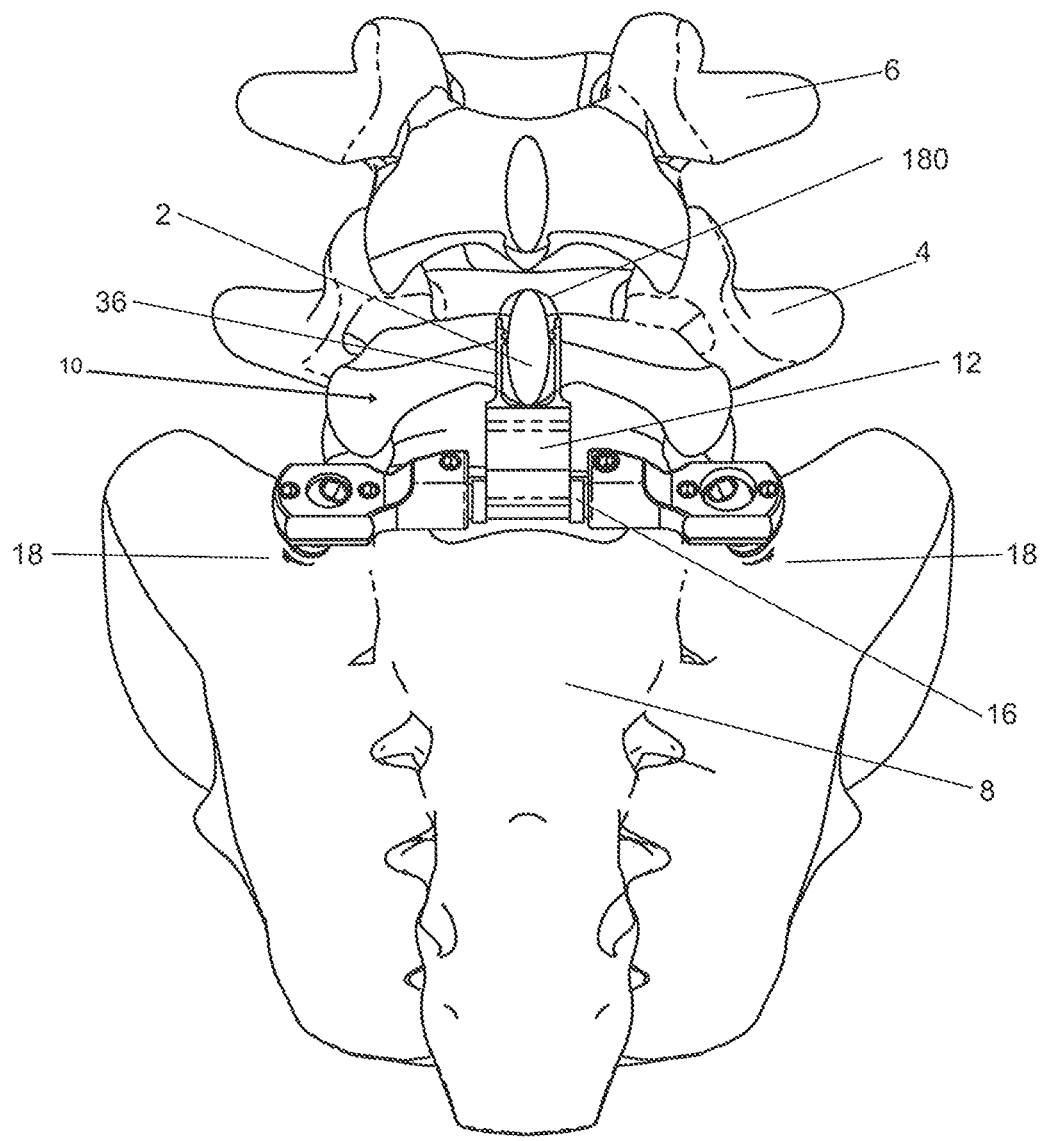
FIG. 17B illustrates the device of FIG. 17A positioned between an L5 spinous process and a sacrum, according to an exemplary disclosed embodiment.

FIG. 17B illustrates the spacer body 12 implanted between a sacrum 8 and spinous process 2 of an adjacent vertebra 4, while the fixation rod 16 is secured to the sacrum 8 using two anchors 18. The lateral walls 36 further secure the spacer body 12 to the spinous process 2 of the vertebra. In addition, the device 10 includes a flexible fixation element 180, which may further secure the device 10 to the spinous process 2.

Figure 18C:
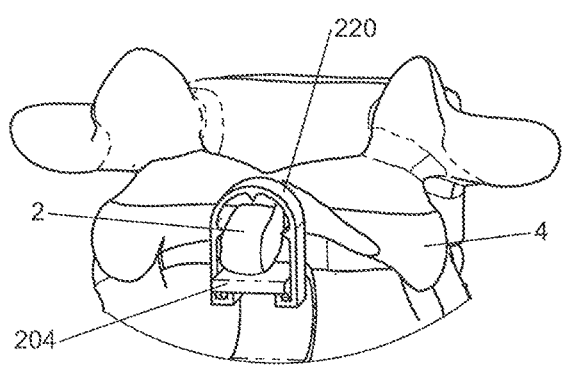
FIG. 18C provides a partial perspective view of the spacer body of FIG. 18A implanted within a patient.
Figure 18A:
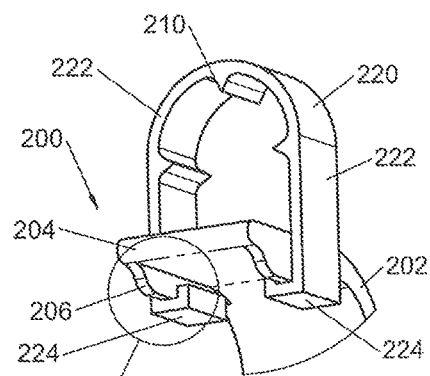
FIG. 18A provides a partial perspective view of a spacer body having a rigid fixation member, according to an exemplary disclosed embodiment.
Figure 18B:
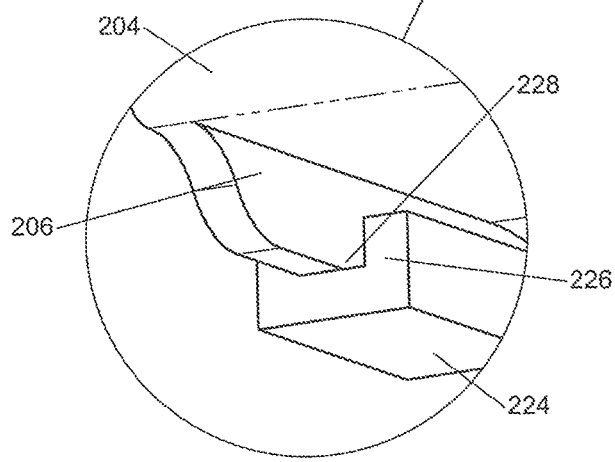
FIG. 18B provides an enlarged view showing details of FIG. 18A.

In still a further exemplary embodiment, as shown in FIGS. 18A-18C and 19A-19C, a rigid fixation element may be used to secure the spacer body to the spinous process. As shown in FIGS. 18A and 18B, a stabilization device 200 is provided which may include a rigid fixation element comprising a rigid fixation cap 220 for placement over a portion of the spacer body 202. The spacer body 202 may be similar to spacer body 12 but without the lateral walls 36. The fixation cap 220 may be U-shaped, and include a pair of sidewalls 222, the terminal ends 224 of which include a lip 226 defining a groove 228 for sliding engagement with a flange 206 on the superior section 204 of the spacer body 202 to securely attach the spacer body 202 to a spinous process 2, as shown in FIG. 18C. The fixation cap 220 can include barbs 210 for secure engagement with the bony surface of the spinous process, thereby ensuring a rigid fixation.

Figure 19A:
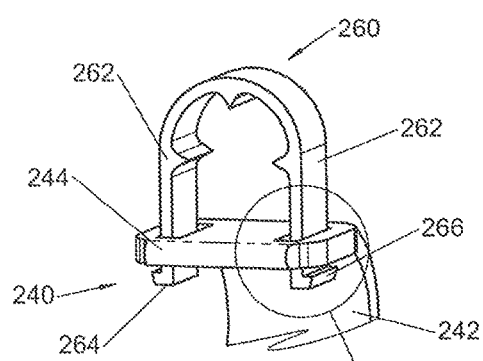
FIG. 19A provides a partial perspective view of a spacer body having a rigid fixation member, according to an exemplary disclosed embodiment.
Figure 19C:
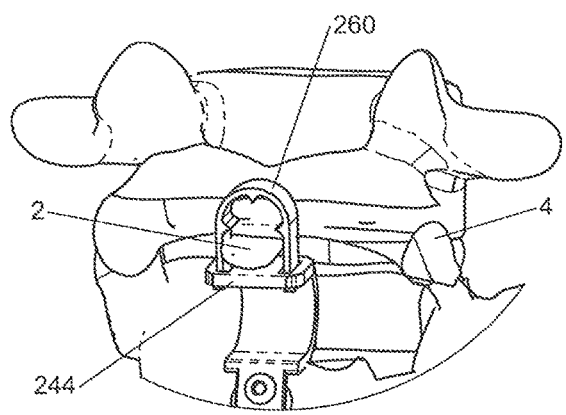
FIG. 19C provides a partial perspective view of the spacer body of FIG. 19A implanted within a patient.
Figure 19B:
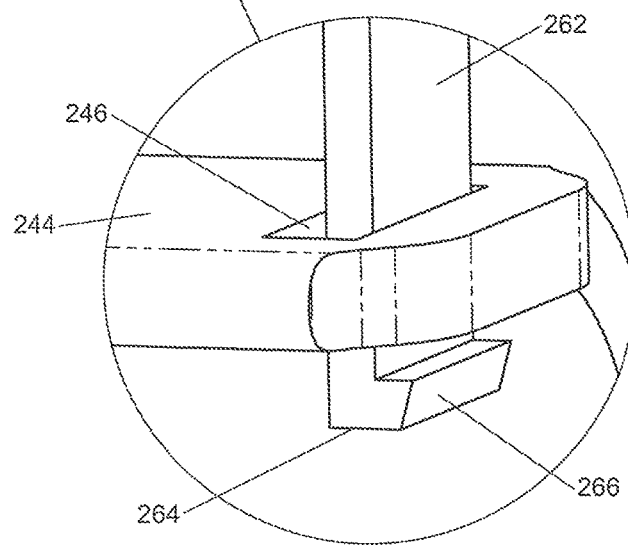
FIG. 19B provides an enlarged view showing details of FIG. 19A.

FIGS. 19A-19C illustrate yet another exemplary embodiment wherein a stabilization device 240 is provided with a rigid fixation element comprising a fixation cap 260 for placement over a portion of the spacer body 242. The fixation cap 260 may be U-shaped, and include a pair of sidewalls 262, the terminal ends 264 of which include a beveled flange 266. Like spacer body 202, the spacer body 242 does not include lateral walls 36. Instead, the spacer body 242 can include slots 246 on the superior section 244. Due to the slight flexibility and compressibility of the sidewalls 262, the beveled flanges 266 can be forced down and through the slots 246, as shown in FIGS. 19A and 19B to engage the spacer body 242. The fixation cap 260 can include barbs 210 for secure engagement with the bony surface of the spinous process, thereby ensuring a rigid fixation.

Figure 20A:
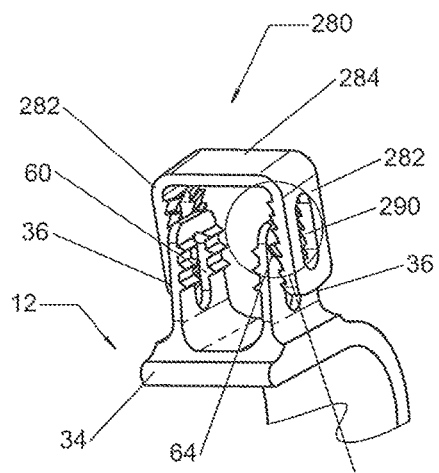
FIG. 20A provides a partial perspective view of a spacer body having a rigid fixation member, according to an exemplary disclosed embodiment.
Figure 20C:
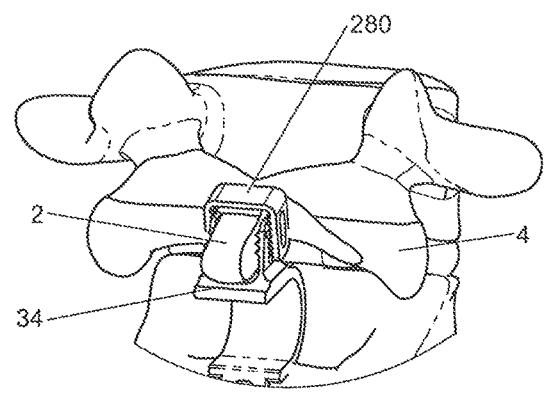
FIG. 20C provides a partial perspective view of the spacer body of FIG. 20A implanted within a patient.
Figure 20B:
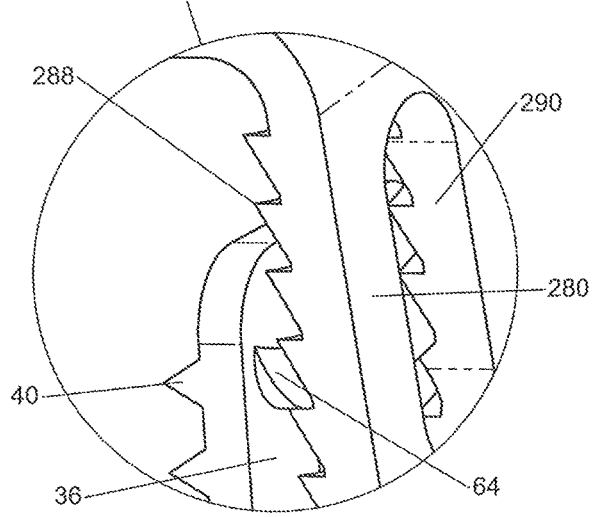
FIG. 20B provides an enlarged view showing details of FIG. 20A.

FIGS. 20A-20C illustrate an exemplary embodiment in which the spacer body 12 of the present invention can be used with a rigid fixation element. As shown in FIGS. 20A and 20B, a rigid fixation cap 280 is provided for use with the spacer body 12 of the present invention. The rigid fixation cap 280 includes a pair of sidewalls 282 connected by a connector section 284. Sidewalls 282 include teeth 288 on an inside surface that can engage a notch 64 on an outer surface on the lateral walls or brackets 36 of spacer body 12. In use, the fixation cap 280 can be placed over the brackets 36 after the spacer body 12 is in position and the vertebra's spinous process 2 resides securely within the stirrup 38 defined by the brackets 36. By pushing downward on the fixation cap 280, the teeth 288 within the sidewalls 282 can ratchet over and lock with the notches 64 of the brackets 36 until the connector section 284 of the cap 280 rests against the spinous process 2, and thereby ensures a secure fit between the bony tissue and the device 10, as illustrated in FIG. 20C. The adjustability of the fixation cap 280 allows the spacer body 12 to secure a variety of sized spinal processes. As shown, the lateral walls or brackets 36 can be provided with elongated slots 60 similar to the elongated slots 290 on the sidewalls 282 of the fixation cap 280. When the fixation cap 280 is ratcheted onto the spacer body 12, the slots 60, 290 align and cooperate to provide an opening for placement of an optional fixation element therethrough for further securement of the spinous process to the spacer body 12, if desired. The fixation element can be, for example, a bolt or bone screw that extends through the spinous process or extends atop the process and across the two sidewalls 282.

The fixation caps 220, 260, 280 may be formed from a variety of different biocompatible metals materials, such as, for example, titanium and stainless steel, or cobalt chrome, or biocompatible plastics, either alone or along with at least one other suitable material from this group. The shape, dimensions, and materials of the fixation caps 220, 260, 280 may be selected to control their physical properties such as flexibility, strength, and/or fracture resistance.

Figure 21:
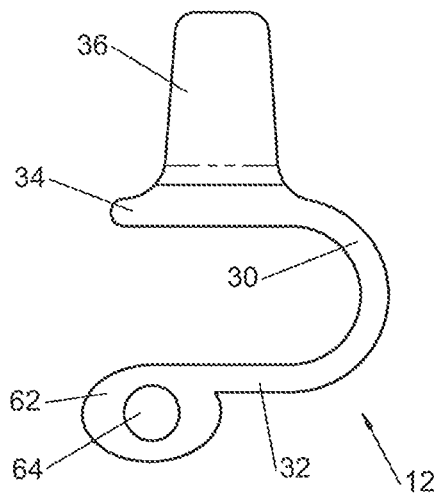
FIG. 21 provides a side view of a spacer body, according to another exemplary disclosed embodiment.

Turning now to the particulars of the anchor assembly 14 and the methods for securing the spacer body 12 to the sacrum, as shown in FIG. 21 the spacer body 12 may connect with the fixation rod 16 at a base portion 62 extending from the inferior section 32. The base portion 62 may form a permanent connection or a removable connection. As illustrated in FIG. 21, the spacer body 12 may include an aperture 64 within the base portion 62 for engaging the fixation rod 16. In one embodiment, the aperture 64 may be a through hole for placement of the fixation rod 16 therethrough. A plastic liner can be provided within the aperture 64 of the base portion 62 to facilitate a smooth, sliding movement of the rod 16 within the aperture 64. The plastic liner can be formed from, for example, a polyethylene, such as ultra high molecular weight polyethylene (UHMWPE), or polyetheretherketone (PEEK).

Figures 22A, 22B:
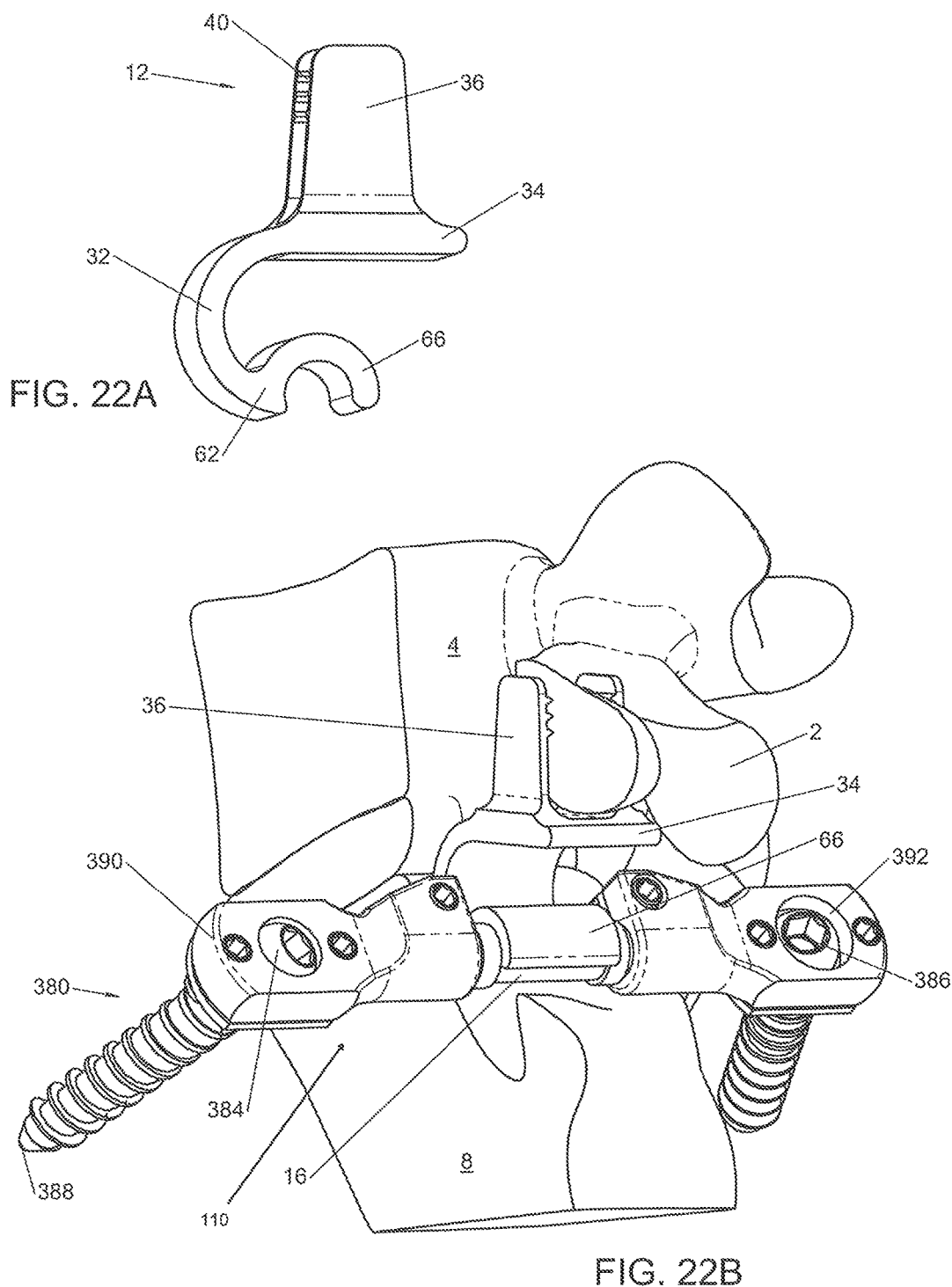
FIG. 22A provides a side perspective view of a spacer body, according to yet another exemplary disclosed embodiment.
FIG. 22B provides a perspective view of the spacer body of FIG. 22A implanted within a patient.

In another embodiment, as shown in FIGS. 22A and 22B, the base portion 62 may comprise a semi-circular or C-shaped section 66 for engaging the fixation rod 16. The C-shaped section 66 can be configured to be snap fitted onto the rod 16. It is contemplated that a plastic liner formed from, for example, a polyethylene, such as ultra high molecular weight polyethylene (UHMWPE) or polyetheretherketone (PEEK) can be provided on the rod 16 between the C-shaped section 66 in order to provide smooth gliding motion of the spacer body 12 against the rod 16.

Figure 23:
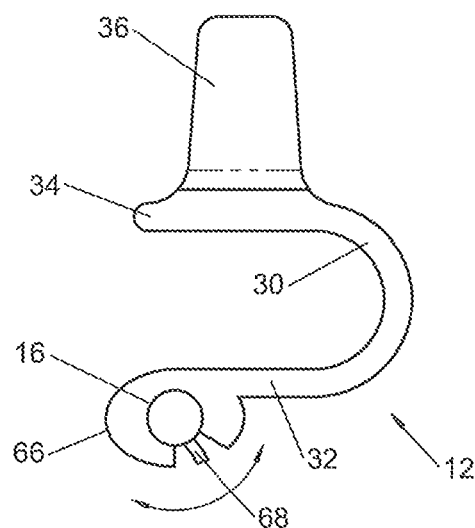
FIG. 23 provides a side view of a spacer body, according to a further exemplary disclosed embodiment.

Further, the spacer body 12 may be configured to be angularly rotatable with respect to the longitudinal axis of the fixation rod 16. In one embodiment, the spacer body 12 may be freely rotatable with respect to the longitudinal axis of the fixation rod 16. In another embodiment, the fixation rod 16 may include one or more protrusions 68 for limiting the rotation of the spacer body 12, as illustrated in FIG. 23. For example, the spacer body 12 may rotate between about 0 and about 60 degrees with the protrusion 68 delimiting the space between which the spacer body 12 can rotate. Such rotation may facilitate positioning of the spacer body 12 during implantation, while also allowing a controlled degree of patient motion after implantation. It is contemplated that the surgeon may select the degree of rotation available by selecting a fixation rod 16 with a protrusion 68 having a predetermined size and shape. Alternatively, the spacer body 12 may be rigidly fixed to the fixation rod 16 so as not to allow any rotation.

Figure 24:
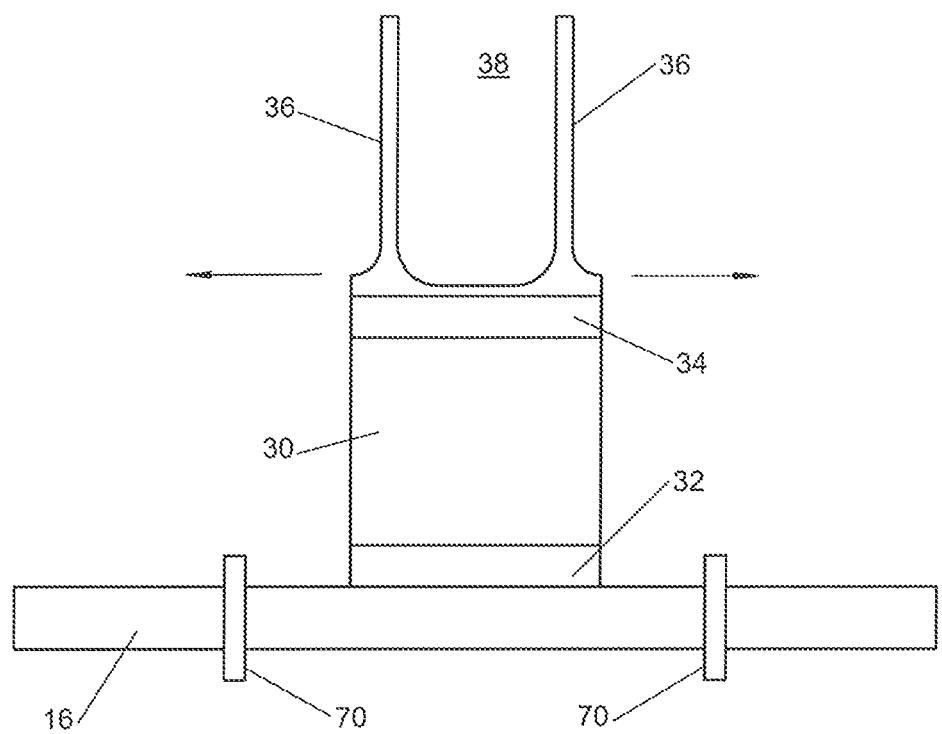
FIG. 24 provides a rear view of a spacer body and fixation rod, according to an exemplary disclosed embodiment.
Figure 26A:
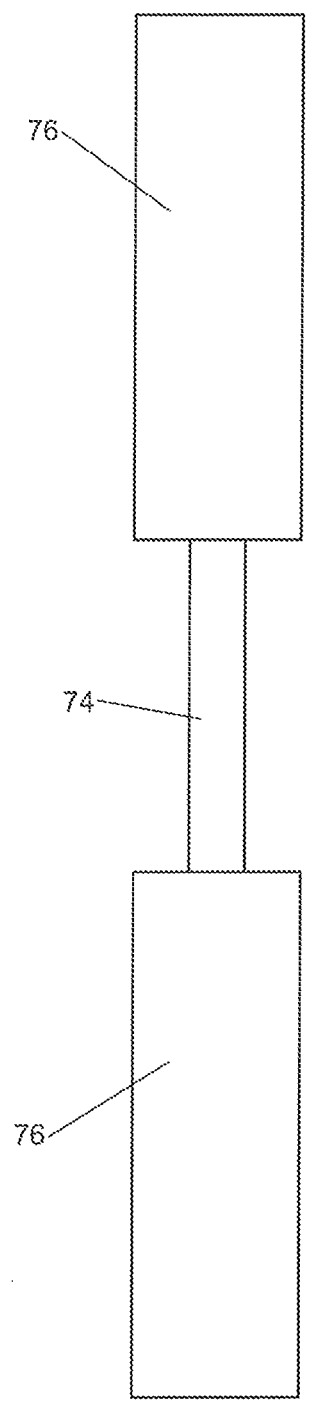
FIG. 26A provides a front view of a fixation rod, according to another exemplary disclosed embodiment.
Figure 26B:
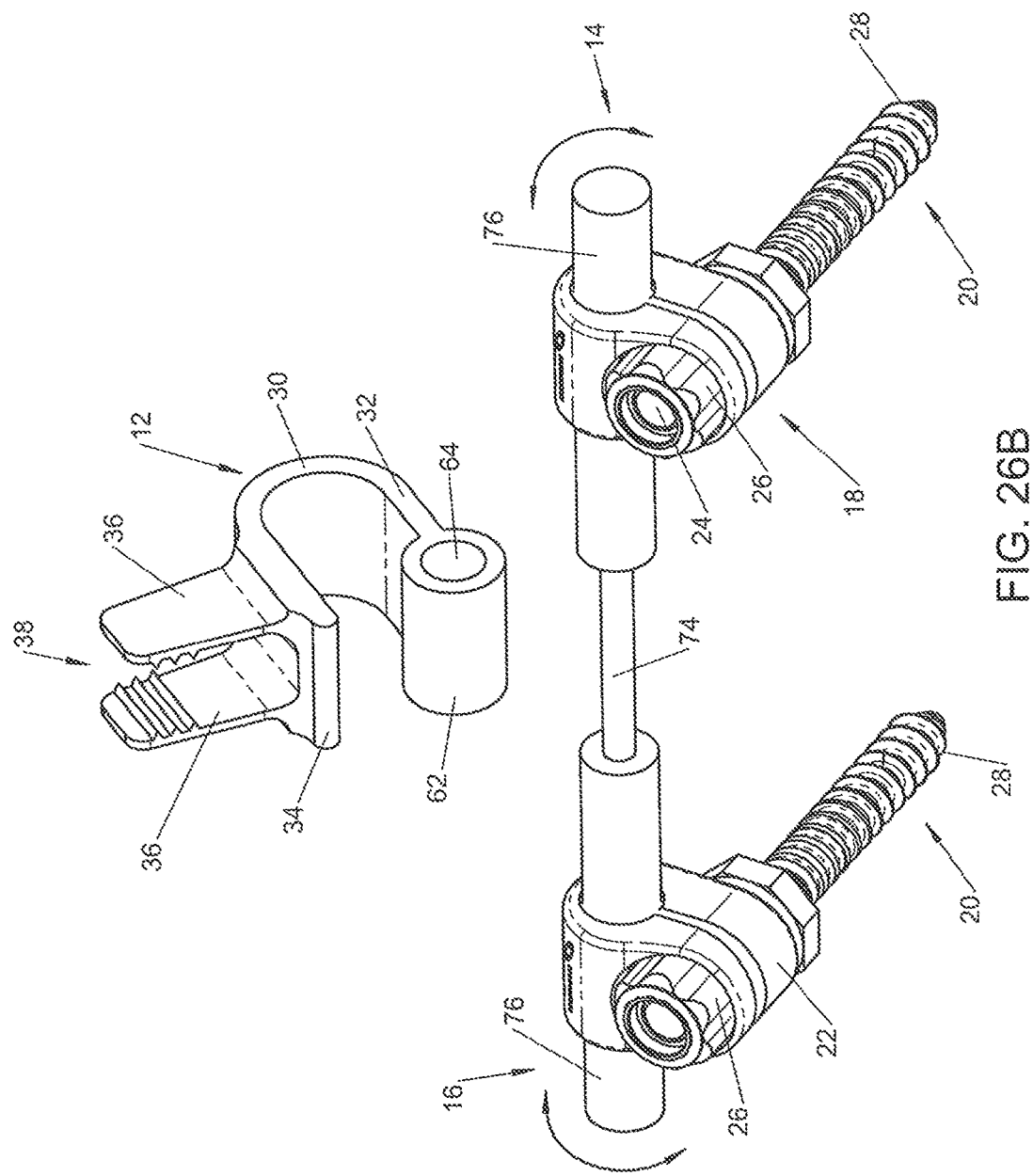
FIG. 26B provides an exploded perspective view of a spacer body and the fixation rod of FIG. 26A, according to an exemplary disclosed embodiment.

In order to allow further flexibility in the orientation of the device 10, either during the implantation process or after implantation, the spacer body 12 may also be configured to be laterally movable or slidable with respect to the fixation rod 16. As shown in FIG. 24, the fixation rod 16 may include one or more lateral protrusions 70 to delimit the space within which the spacer body 12 can slide. Thus, the lateral protrusions 70 may limit lateral displacement of the spacer body 12 when attached to the fixation rod 16. In one embodiment, the lateral protrusions 70 may be adjustably positioned on the fixation rod 16, thereby allowing the surgeon to select a desired degree of lateral displacement. Further, in one embodiment, the lateral protrusions 70 may be positioned adjacent the spacer body 12 to prevent any lateral movement of the spacer body 12 with respect to the fixation rod 16. Alternatively, fixation rod 16 may be configured to limit lateral movement of the spacer body 12 (as shown in FIGS. 26A and 26B).

Figure 25A:
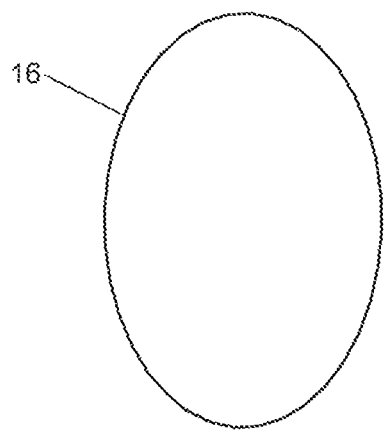
FIGS. 25A-25C provide cross-sectional views of fixation rods, according to exemplary disclosed embodiments.
Figure 25B:
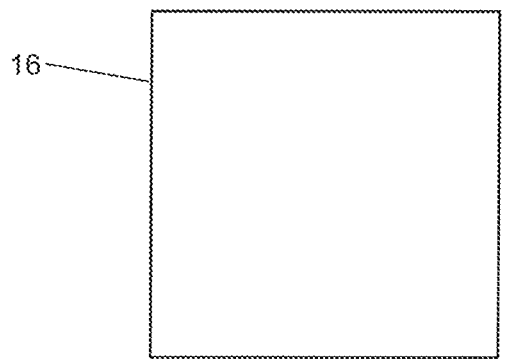
Figure 25C:
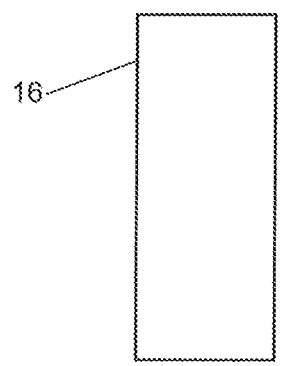

Turning now in particular to the fixation rod 16, the fixation rod 16 may be configured to have a number of different shapes, sizes, and/or material properties. In the embodiment of FIG. 1, the fixation rod 16 is a straight rod with a circular cross-section. FIGS. 25A-25C illustrate additional cross-sectional geometries suitable for the fixation rod 16 of the present disclosure. For example, the fixation rod 16 may have an oval cross-section (FIG. 25A), a square cross-section (FIG. 25B), or a rectangular cross-section (FIG. 25C).

In addition, the fixation rod 16 may have a cross-sectional geometry that is variable across its length. For example, as shown in FIG. 26A, the fixation rod 16 may include a connecting region 74 for engaging the base portion 62 of the spacer body 12. The connecting region 74 may be thicker or thinner (as shown in FIGS. 26A and 26B) than the surrounding thicker sections 76 of the fixation rod 16.

In one embodiment, the fixation rod 16 may be configured to limit lateral movement of the spacer body 12. For example, as shown in FIG. 26B, the fixation rod 16 may include a narrow connecting region 74. During production, the spacer body 12 may be connected to the fixation rod 16 at the narrow connecting region 74 by engaging the base portion 62 thru the aperture 64. The surrounding thicker sections 76 may thereby block lateral movement of the spacer body 12 on the fixation rod 16, while still allowing rotation of the spacer body 12 with respect to the fixation rod 16. Alternatively or in addition, the spacer body 12 may be fused to the fixation rod 16 to prevent lateral movement and/or rotation with respect to the fixation rod 16.

Like the spacer body 12, the fixation rod 16 may be formed from a variety of different biocompatible materials. For example, the fixation rod 16 may, e.g., be formed from titanium, stainless steel, ceramics, or cobalt chrome, either alone or along with at least one other suitable material from this group. The fixation rod 16 may comprise the same materials as the spacer body 12 or different materials than the spacer body 12. The shape, dimensions, and materials of the fixation rod 16 may be selected to control the flexibility, strength, and/or fracture resistance of the fixation rod 16. The length and thickness may also be selected based on a patient's size, disease characteristics, and/or activity level.

Figure 27A:
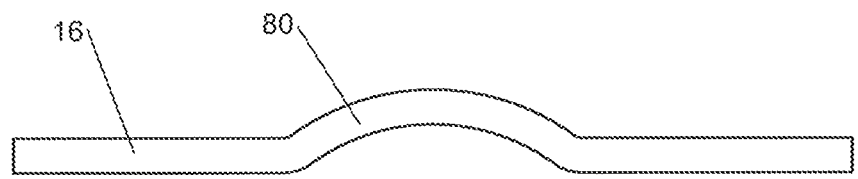
FIGS. 27A-27C illustrate front views of alternate fixation rods, according to exemplary disclosed embodiments.
Figure 27B:
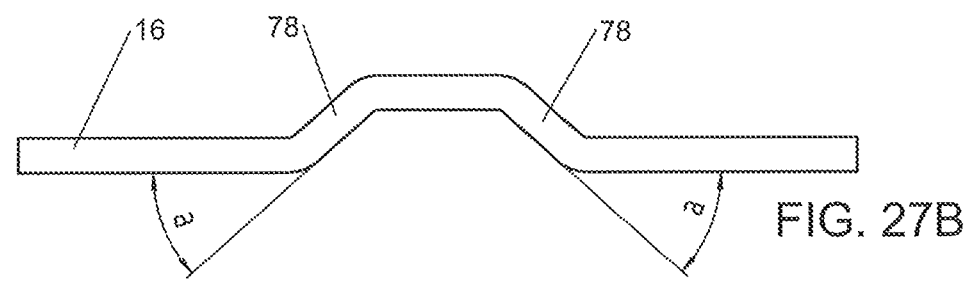
Figure 27C:
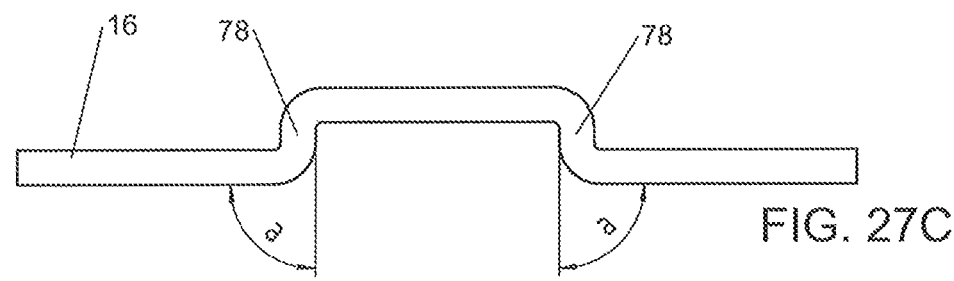

As shown in FIGS. 27A-27C, the fixation rod 16 may be straight, bent, or curved along its length to accommodate the natural curves of the patient's anatomy. For example, in one embodiment, the fixation rod 16 may include at least one curved section 80 (FIG. 27A). In another embodiment, the fixation rod 16 may include at least two bent sections 78 (FIG. 27B). The bent sections 78 may be formed at an angle a with respect to a longitudinal axis of the fixation rod 16. The angle a may be between 0 and 90 degrees. For example, the angle a may be about 30 degrees (FIG. 27B) or about 90 degrees (FIG. 27C).

In use, the fixation rod 16 having a curved 80 or bent section 78 may be implanted in a number of different anatomic orientations. For example, the bent section 78 may be positioned in a superior-anterior orientation with respect to the longitudinal axis of the fixation rod 16. The exact orientation may be selected based on surgical factors and/or patient anatomy.

Figure 28A:
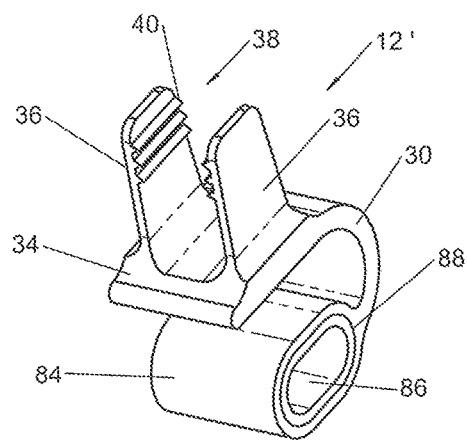
FIG. 28A provides a perspective view of a spacer body, according to an exemplary disclosed embodiment.
Figure 28B:
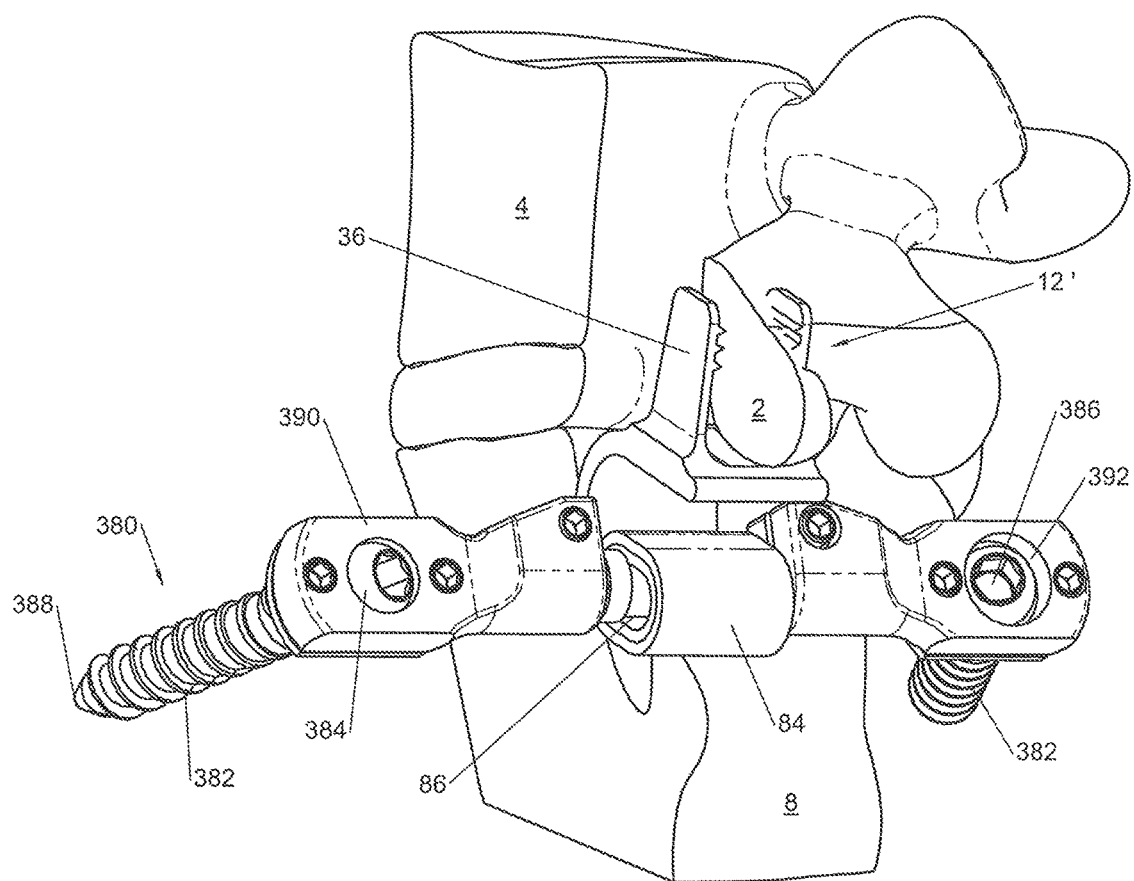
FIG. 28B provides a perspective view of a device including the spacer body of FIG. 28A, implanted in a patient.

In some situations, it may be desirable to provide a spacer body 12' which can slide not only laterally but in the anterior-posterior direction as well. FIGS. 28A and 28B provide such an exemplary embodiment, in which the spacer body 12' includes an elongate or oval base portion 84 with a corresponding elongate or oval aperture 86 for use with a cylindrical rod 16 of the present invention. In all other aspects, spacer body 12' is similar to spacer body 12 previously described, whereby similar features are designated by the same reference numerals. To facilitate a smooth gliding motion between the base portion 84 and rod 16, a plastic liner 88 can be provided within the aperture 86. The plastic liner can be formed from any suitable plastic, such as, for example, ultra high molecular weight polyethylene (UHMWPE) or polyetheretherketone (PEEK). When implanted within a patient, the elongate base portion 84 provides sufficient clearance for the spacer body 12 to glide back and forth in an anterior to posterior direction during flexion and extension of the vertebral column.

Figure 29A:
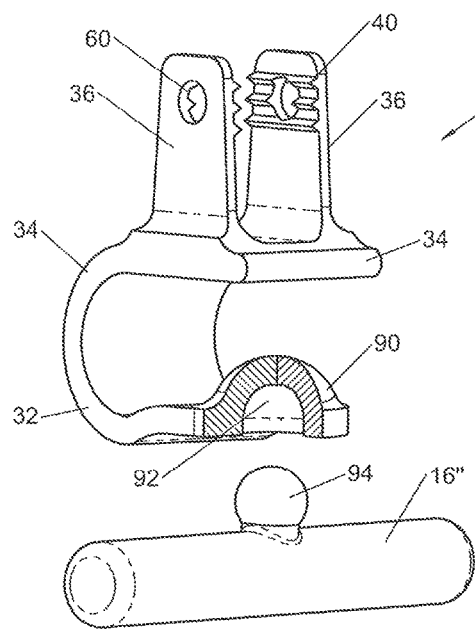
FIG. 29A provides an exploded view of a spacer body and rod, according to an exemplary disclosed embodiment.
Figure 29B:
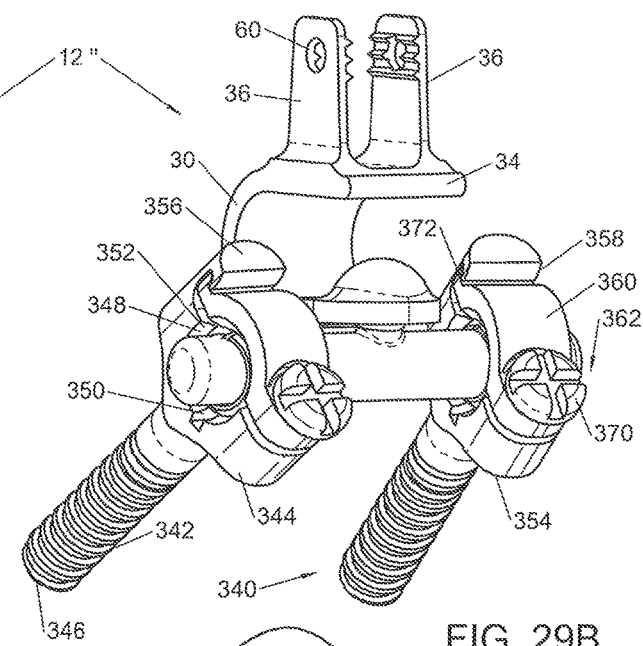
FIG. 29B provides a perspective view of a device including the spacer body and rod of FIG. 29A.
Figure 29C:
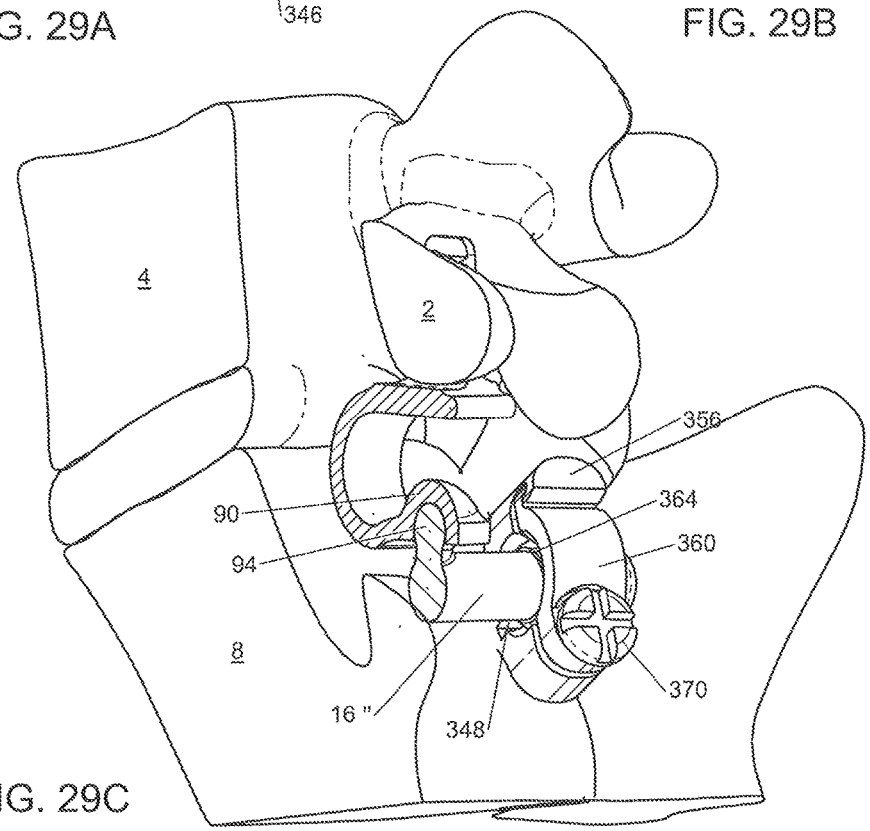
FIG. 29C provides a partial cross-sectional view of the device of FIG. 29B implanted in a patient.

FIGS. 29A-29C illustrate yet another exemplary embodiment of a spacer body 12" which can translate about the anterior-lateral direction with respect to the fixation rod 16". As shown in FIG. 29A, the spacer body 12" includes an inferior section 32 having a raised socket 90 defining a spherical groove or cavity thereunder 92. The spherical cavity 92 is configured to sit against a spherical protrusion or knob 94 on fixation rod 16". In all other aspects, the spacer body 12" and the fixation rod 16" are similar to the spacer body 12 and fixation rod 16 previously described, whereby similar features are designated by the same reference numerals. In use, the raised socket 90 is positioned over and sits on the spherical protrusion or knob 94, creating a ball-and-socket type joint. Such a connection would allow the spacer body 12" to rotate freely with respect to the rod 16" and thereby provide the patient with even greater flexibility and degree of motion, especially during twisting or bending movements, but still providing a rigid, fixed attachment to the vertebra being supported.

Figure 30:
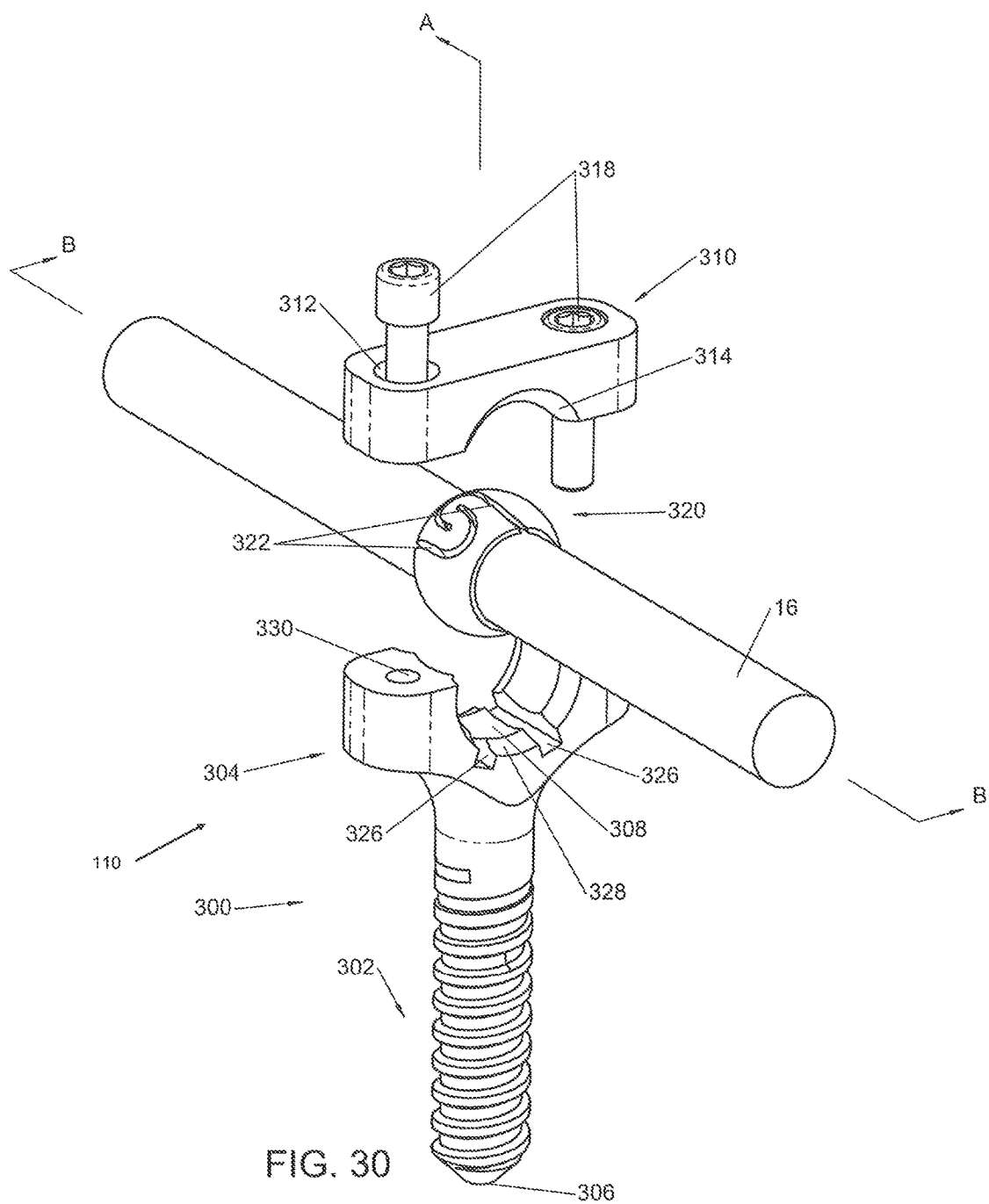
FIG. 30 provides an exploded perspective view of a polyaxial screw system, according to an exemplary disclosed embodiment.

To secure the fixation rod 16 to the patient's sacrum or other bone surface, fixation elements may be provided. The fixation elements may include anchors 18 that attach to the fixation rod 16 at one or more anchor-connecting regions 110. Anchor-connecting regions 110 may include protrusions, as illustrated in FIG. 30. Additionally, the anchor-connecting regions 110 may comprise indentations, concavities, convexities, or anchor through-holes, as shown in FIG. 22B. The design of anchor-connecting regions 110 may be selected based on the design of the particular type of anchor 18 being used. It is contemplated that the design and type of anchor 18 can vary without departing from the spirit of the present disclosure. For example, the anchors 18 may include any type of screw that may securely engage bone.

Turning now to the particulars of the fixation element or anchor 18 shown in FIG. 1, the anchor 18 may comprise a polyaxial screw, which may be aligned in a range of angular orientations with respect to the fixation rod 16. Thus, the polyaxial screws may allow the surgeon to easily adjust the position of the screw during surgery and consequently the fixation rod 16 based on anatomic variances of the patient.

In one exemplary embodiment, the anchor 18 can be similar to the one disclosed in U.S. Pat. No. 6,554,831 to Rivard, which is hereby incorporated in its entirety by reference. As shown in FIGS. 1 and 26B, the polyaxial screw 20 is captured within a C-shaped collar such as clamp collar 22 that fits around the fixation rod 16. The screw 20 can include a proximal threaded portion 24 that extends through the collar 22 and is fixed in place by tightening nut 26, and a distal threaded portion 28 that enables the screw 20 to anchor to bone tissue.

It is understood, of course, that a number of differently designed polyaxial screws may be used with the present invention in order to provide the surgeon with the ability to secure the fixation rod 16 to the patient in an effective manner. An exemplary embodiment of a polyaxial screw 300 suitable for use with the present invention is shown in FIGS. 30, 31A and 31B. As illustrated, the polyaxial screw 300 includes an elongated threaded body 302 extending between a head portion 304 and a distal end 306. The threaded body 302 can be straight or angled or curved, depending on the particular need of the patient. The head portion 304 includes a hollow spherical cavity 308 for receiving an anchor-connecting element, which in this embodiment takes the form of a spherical clamp ring 320. The spherical clamp ring 320 includes slots 322 distributed around its periphery to enable the clamp ring 320 to flex and slidingly fit over a fixation rod 16.

The head 304 also includes a plurality of spherical undercuts 328, creating curved inclined walls, and slots 326 extending therein at the bottom of the cavity 308, which are disposed so that they are substantially radial in relation to the cavity 308. These slots 326 and undercuts 328 converge toward one another in the direction of the bottom of the cavity 308 and give a slight flexibility to the head 304. In addition, the undercuts 328 enable the slotted spherical clamp ring 320 to snap on inside the hollow spherical cavity 308. Two threaded holes 330 are also provided on the head portion 304 for receiving threaded screws 318.

A locking cap 310 is provided which comprises screw holes 312 for receiving the threaded screws 318. The screw holes 312 coincide with the holes 330 on the head portion 304. The locking cap 310 also includes a hollow cavity 314 suitably shaped to receive a portion of the spherical clamp ring 320, as illustrated in FIG. 31A. For example, the hollow cavity 314 can have a cone shape, permitting the cap 310 to come into contact with the spherical clamp ring 320 in the course of tightening the screws 318. The hollow cavity 314 can also include lateral undercuts and slots similar to those present in the spherical cavity 308 of the head portion 304 to enable the screw 300 to adjust angularly prior to being locked together, as shown in FIG. 31B.

In use, the spherical clamp ring 320 is snap-fitted onto the hollow cavity 308 of the head portion 304 of the screw 300, the clamp ring 320 being held by the engagement of the slots 322 of the clamp ring 320 and the undercuts 328 of the head portion 304. The clamp ring 320 with the head portion 304 and threaded body 302 is then slid over the fixation rod 16 and positioned at an anchor-connecting region of the rod 16. The cap 310 is then positioned over the clamp ring 320 and the threaded screws 318 inserted through the screw holes 312, 330 and tightened. The entire process can be repeated, since a plurality of screws 300 can be used with any given fixation rod 16, depending on the needs of the patient.

In FIG. 29B, a similar polyaxial screw 340 is shown, but with a modified head portion 344. Like the polyaxial screw 300 previously described, polyaxial screw 340 includes an elongated threaded body 342 extending between a head portion 344 and a distal end 346. The threaded body 342 can be straight or angled or curved, depending on the particular need of the patient. The head portion 344 includes a hollow spherical cavity 348 for receiving an anchor-connecting element, such as, for example, the spherical clamp ring 320 of FIG. 30. As with the previous embodiment, the head portion 344 can include a plurality of spherical undercuts 352, creating curved inclined walls, and slots 350 extending therein at the bottom of the cavity 348. A threaded hole 354 is also provided on the head portion 344 for receiving a threaded screw 370. At an opposite end of the head portion 344 is a raised flange 356 which creates a groove 358 for slidingly receiving a locking cap 360, as shown in FIGS. 29B and 29C.

Locking cap 360 is provided with a lip 372 at one end and at an opposite end a single screw hole 362 for receiving the threaded screw 370. The screw hole 362 coincides with the hole 354 on the head portion 344. The lip 372 enables the cap 360 to slide over the head portion 344 and engage with the groove 358 prior to insertion of the threaded screw 370. The lip 372 of the locking cap 360 and corresponding groove 358 of the head portion 344 can be configured to provide a slight gap or clearance sufficient for the locking cap 360 to be able to flip up to about a 90.degree. angle with respect to the head portion 344 without becoming dislodged, thereby creating a hinge between the cap 360 and the head portion 344. Alternatively, the locking cap can be configured to attach to the head portion via a hinge joint. Further, as with the previously described embodiment, the locking cap 360 can also include a hollow cavity 364 suitably shaped to receive a portion of the anchor-connecting element 110, which hollow cavity 364 can also include lateral undercuts and slots similar to those present in locking cap 310.

Yet another exemplary embodiment of a polyaxial screw 380 suitable for use with the devices 10 of the present invention is shown in FIGS. 22B and 28B. In these embodiments, fixation rod 16 can be attached at both ends to a plate 390 having a spherical countersink 392 with a through-hole for insertion of the polyaxial screw 380 therethrough. The plate 390 can be clamped onto the rod 16, or it can be configured with an aperture for sliding engagement of the rod 16 into the plate 390 itself. The polyaxial screw 380 includes an elongate threaded body 382 extending from a spherical head 384 into a distal end 388. The spherical head 384 includes a hexagonal opening 386 for receiving an insertion tool (not shown). In use, the spherical head 384 of the polyaxial screw 380 can be angularly adjustable within the spherical countersink 392 of the plate 390 prior to being secured to bone tissue.

Figure 32A:
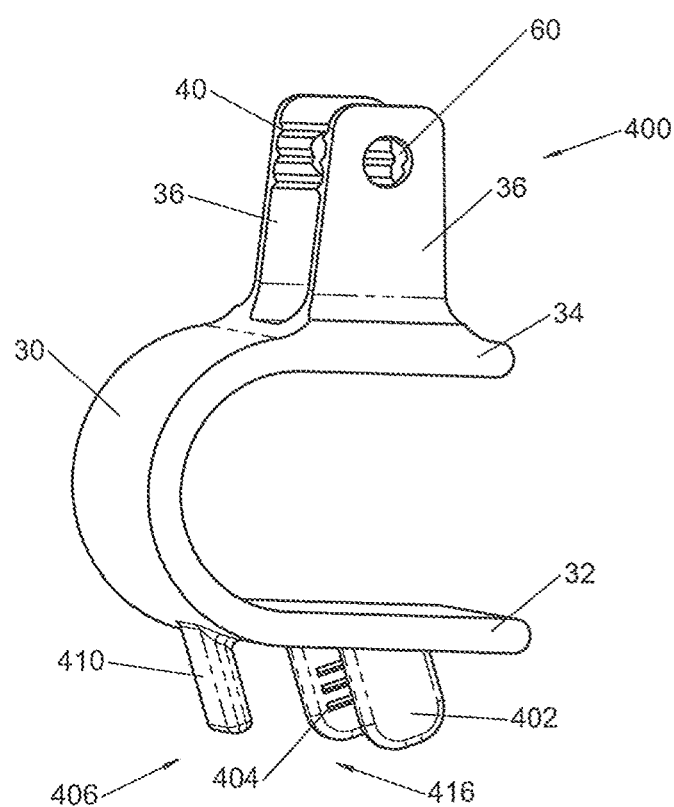
FIG. 32A provides a side perspective view of a spacer body, according to an exemplary disclosed embodiment.
Figure 32B:
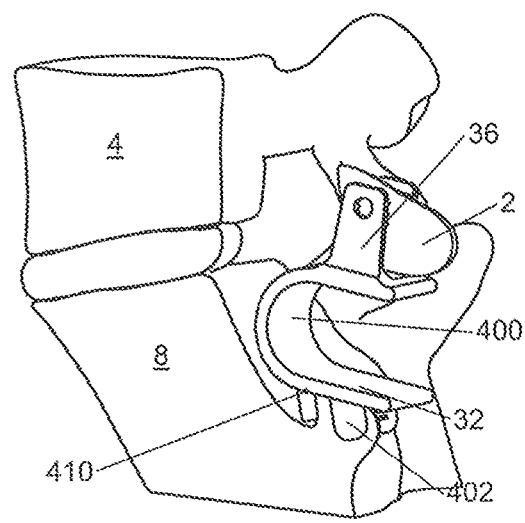
FIG. 32B provides a partial side perspective view of the spacer body of FIG. 32A implanted in a patient.

While rod-based systems have been described for anchoring the spacer body 12 to the sacrum or other bone tissue, FIGS. 32A-41 provide additional exemplary embodiments of spacer bodies that do not require a rod to be attached to the sacrum. In FIG. 32A, a spacer body 400 is shown having similar features to the spacer body 12 of previously described embodiments, wherein the same features are designated by the same reference numeral. Spacer body 400 includes a pair of angled legs 402 extending from the inferior section 32 of the spacer body 400. The legs 402 lie in a plane that is substantially parallel to the planes containing the brackets 36, and can include surface features such as, for example, barbs 404 for engagement with bone tissue. The legs 402 collectively form an anchor assembly 406 portion comprising a gripping portion 416 for attachment to the sacrum. A backplate 410 can optionally be provided which extends from the inferior section 32 and lies in a plane that intersects with the planes containing the brackets 36. In use, the legs 402 are configured to rest against the median crest of the sacrum 8, while the backplate 410 rests within the sacral canal and against the sacrum 8, as shown in FIG. 32B. Thus, the legs 402 and backplate 410 provides a passive bone-engaging region which allows the spacer body 400 to be inserted and secured onto the sacrum without the need for injury or trauma to the bone resulting from screw fixation.

Figure 33A:
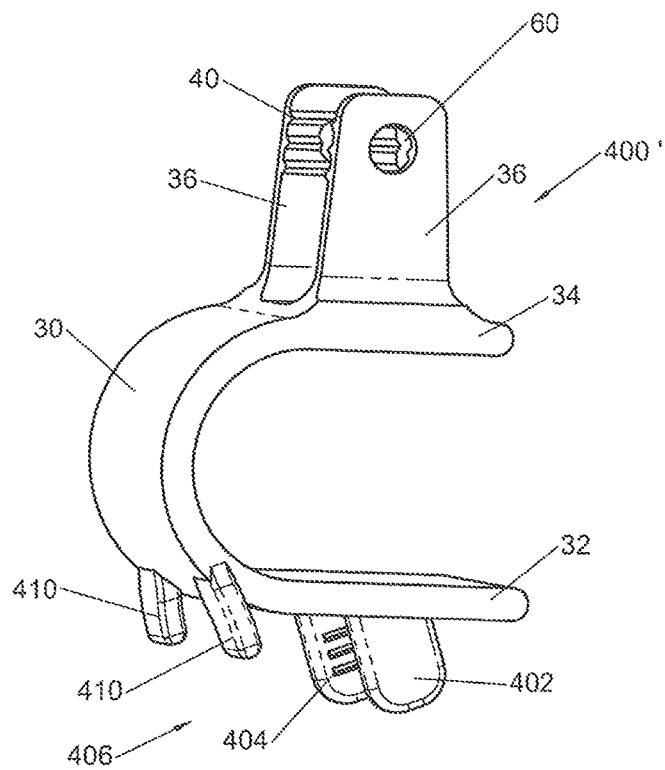
FIG. 33A provides a side perspective view of a spacer body, according to an exemplary disclosed embodiment.
Figure 33B:
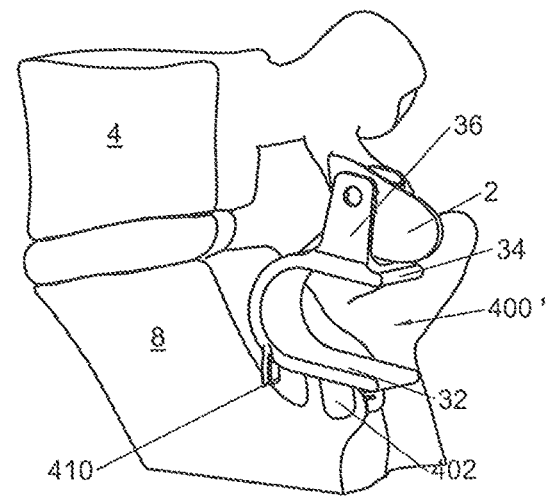
FIG. 33B provides a partial side perspective view of the spacer body of FIG. 33A implanted in a patient.

In FIG. 33A, a spacer body 400' is shown having an anchor assembly 406 comprising two backplates 410 extending from the inferior section 32 at an angle away from one another. Each of the backplates 410 can also be slightly curved along its longitudinal axis. As shown in FIG. 33B, when in use the spacer body 400' rests against the sacrum such that the two backplates 410 rest against the sacrum inside the sacral canal, and legs 402 hook onto the median crest of the sacrum 8. The two backplates 410 are configured to provide sufficient clearance between them so as to avoid impinging any nerve tissue contained within the sacral canal once they are inserted into the canal.

Figure 34A:
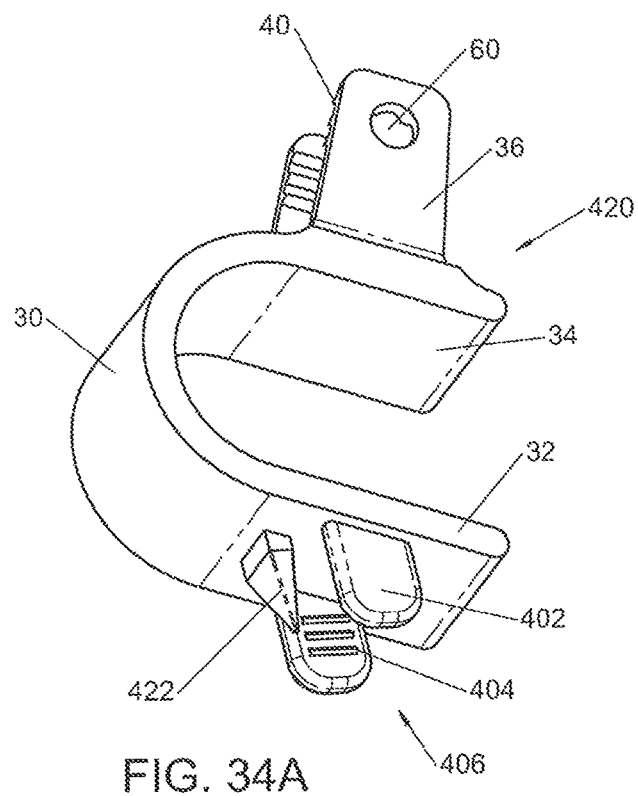
FIG. 34A provides a side perspective view of a spacer body, according to an exemplary disclosed embodiment.
Figure 34B:
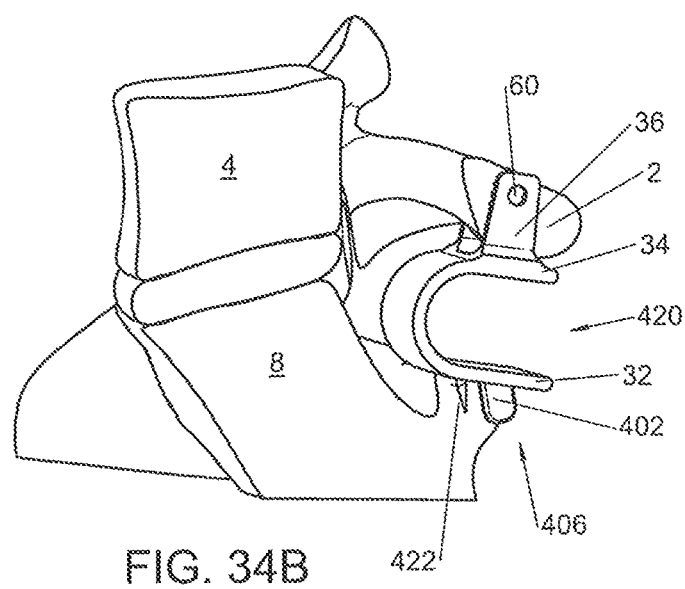
FIG. 34B provides a partial side perspective view of the spacer body of FIG. 34A implanted in a patient.

Instead of having a backplate 410, the spacer body 420 of FIG. 34A includes an anchor assembly 406 comprising a spike 422 extending from the inferior portion 32 at an angle generally parallel to the legs 402. The spike 422 can have a sharp pointed tip, as shown. In use, the spike 422 is configured to pierce into the sacral bone tissue while the legs 402 engage the median crest, thereby allowing the spacer body 420 to be in position and rest on the sacrum, as illustrated in FIG. 34B. Although the legs 402 of the present embodiments are shown as plates extending from the spacer body, it is contemplated that the legs 402 can comprise hooks, barbs, jaws, or any suitable gripping element.

Figure 35A:
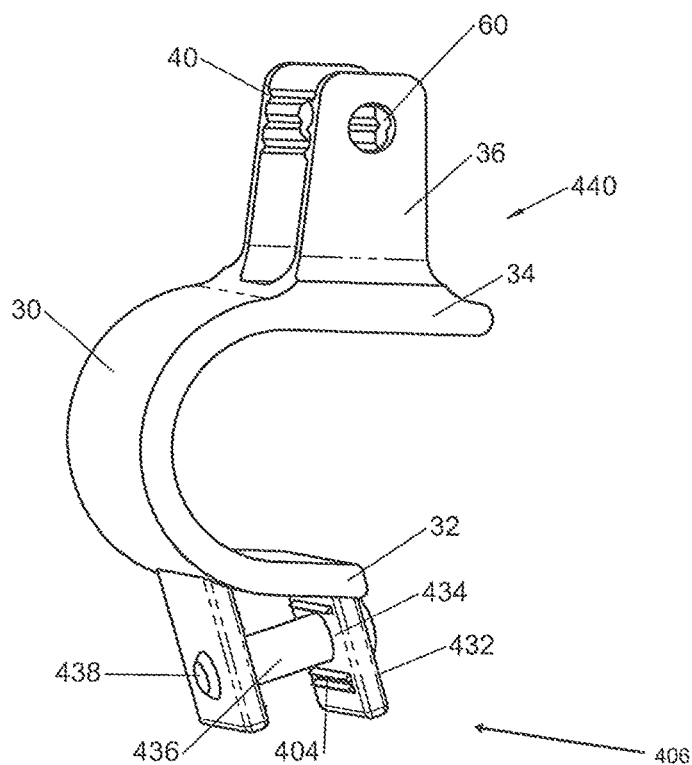
FIG. 35A provides a side perspective view of a spacer body, according to an exemplary disclosed embodiment.
Figure 35B:
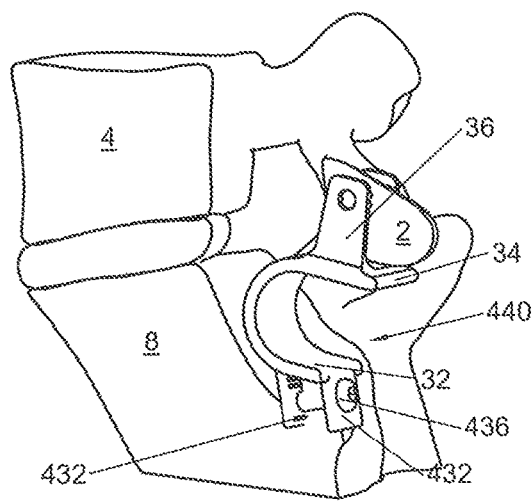
FIG. 35B provides a partial side perspective view of the spacer body of FIG. 35A implanted in a patient.

FIGS. 35A and 35B show yet another exemplary embodiment of a spacer body 440 which includes an anchor assembly 406 comprising a pair of endplates 432 extending from the inferior section 32 of the spacer body 430, each endplate 432 having a screw hole 434 for insertion of a screw 436 therethrough. In use, the endplates 432 can be positioned between the sacral canal and the outer surface of the sacrum, and a screw 436 placed through the bone tissue and secured through the endplates 432 with a nut 438. It is contemplated that more than one screw 436 may be implemented in the present embodiment. For example, the endplates 432 may be configured to allow for two or more screws 436 to be placed in any suitable orientation relative to one another, such as in a horizontal or longitudinal row. Alternatively, two or more screws 436 may be inserted through the endplates 432 such that screws 436 flank the median sacral crest. In one embodiment, the spacer body 430 can be provided with two pairs of endplates 432, with each pair of endplates being configured to grip onto a portion of the sacrum, the two pairs of endplates flanking the median sacral crest. The endplates 432 may, of course, be provided with any suitable number of screw holes for insertion of bone screws 436 therethrough. Such embodiments would provide rigid and secure fixation of the spacer body 430 to the sacrum.

Figures 36A, 36B:
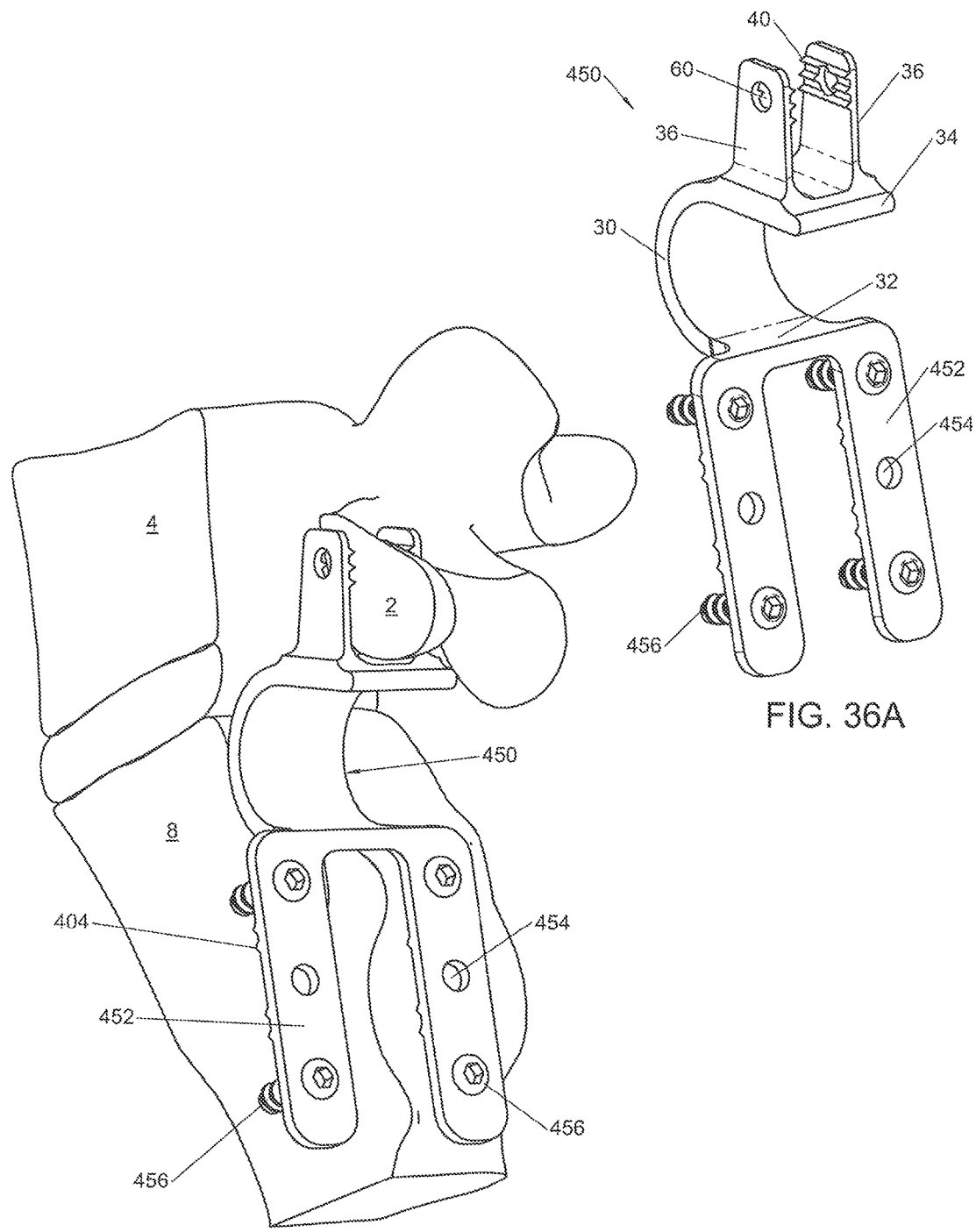
FIG. 36A provides a side perspective view of a spacer body, according to an exemplary disclosed embodiment.
FIG. 36B provides a partial side perspective view of the spacer body of FIG. 36A implanted in a patient.

Rather than having two endplates 432, FIGS. 36A and 36B show an exemplary embodiment in which the spacer body 450 includes a single endplate 452 extending at about a 90.degree. angle with respect to the inferior section 32 of the spacer body 450. As shown, the endplate 452 can include barbs 404 and a plurality of screw holes 454 for placement of screws 456 therethrough. The endplate 452 can be configured with a substantially U-shaped body and a pair or more of screw holes 454 extending along the length of each leg of the U. The opening provided by the U-shape allows the endplate 452 to accommodate the spinous process, thereby avoiding the need to resect any part of the bone tissue. Of course, it is understood that the endplate 452 can take any shape and/or size suitable for placement against a sacral surface, and that any number of screws 456 can be applied in order to achieve a rigid and secure fixation to the bone tissue. In use, the endplate 452 is configured to rest against the outer surface of the sacrum 8 when the spacer body 450 is in position within the patient, as shown in FIG. 36B.

Figures 37A, 37B:
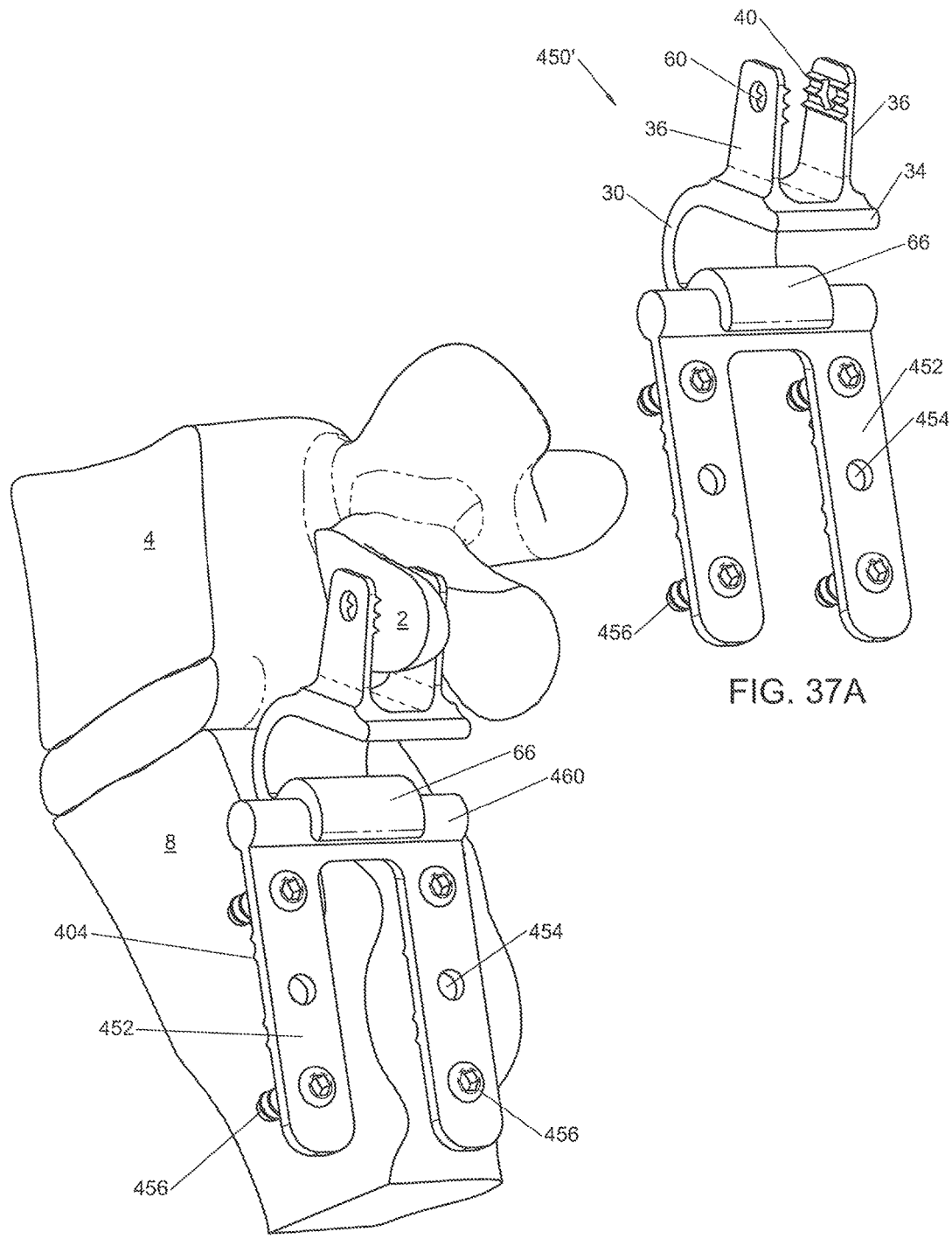
FIG. 37A provides a side perspective view of a spacer body, according to yet another exemplary disclosed embodiment.
FIG. 37B provides a partial side perspective view of the spacer body of FIG. 37A implanted in a patient.

FIGS. 37A and 37B show still yet another exemplary embodiment in which the spacer body 450' has a detachable endplate 452. The spacer body 450' has a shape similar to that shown in FIG. 22A, with the base portion 62 having a C-shaped claw section 66 for snap fitting onto a rod-like attachment end 460 of the detachable endplate 452. Such a configuration would enable the endplate 452 to be rotatable with respect to the spacer body 450' and thereby provide flexibility for the surgeon during implantation. A plastic liner formed from, for example, a polyethylene, such as ultra high molecular weight polyethylene (UHMWPE), or polyetheretherketone (PEEK) can be provided between the rod-like attachment end 460 and the C-shaped section 66, in order to provide smooth gliding motion of the spacer body 12 against the plate 452.

Figure 38A:
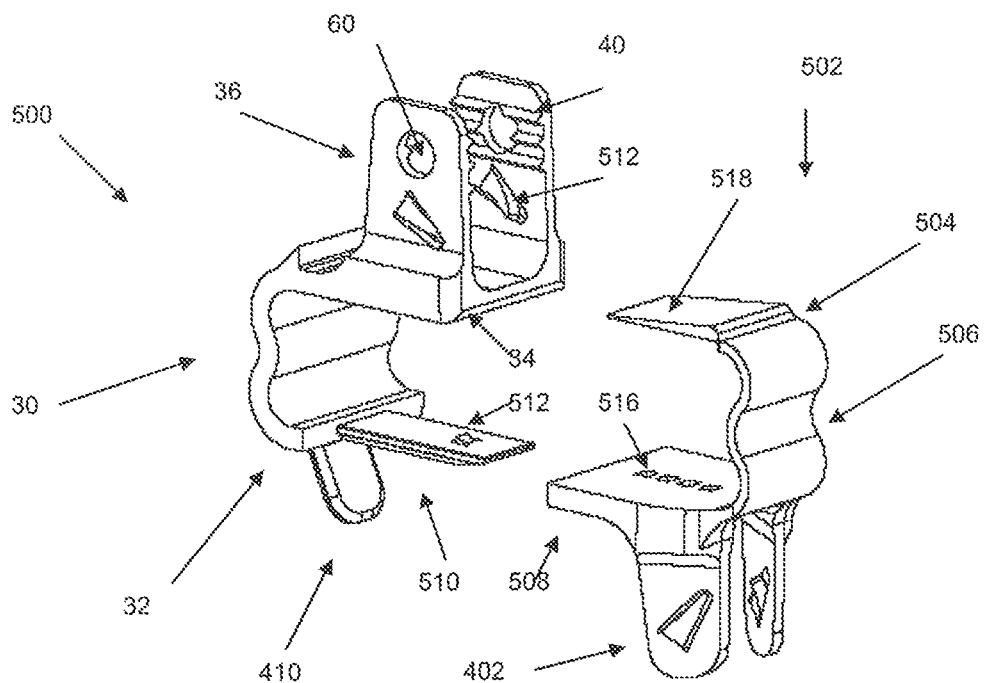
FIG. 38A provides an exploded perspective view of a spacer body, according to another exemplary disclosed embodiment.
Figure 38B:
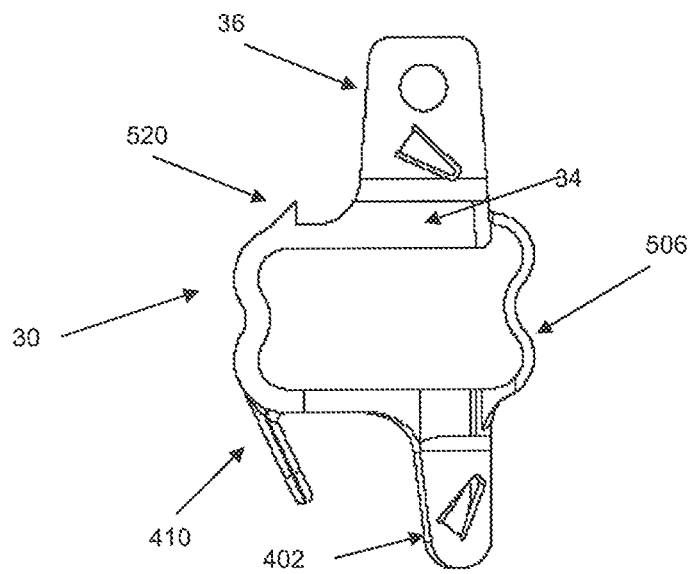
FIG. 38B provides a side perspective view of the spacer body of FIG. 38A assembled.

FIGS. 38A and 38B show an exemplary embodiment in which the spacer body 500 can include a midsection 30, inferior 32 and superior 34 sections, and lateral walls or brackets 36 similar to spacer bodies previously described and shown. As previously discussed, the midsection 30 may have varying thickness or dimensions along its length to provide varying physical properties, or may be shaped or curved as shown, in order to better adapt to the anatomical features of the patient. The lateral walls or brackets 36 may include an aperture 60 for receiving a fastener such as, for example, a rivet. Further, the spacer body 500 may also include surface alterations such as barbs or teeth 40, 512 to facilitate tissue attachment, bonding or fixation. At least one backplate 410 may extend from the inferior section 32. The backplate 410 may be positioned within the sacral canal and against the sacrum when implanted.

A side cap or panel 502 may be provided for attachment to the spacer body 500. The side cap or panel 502 may include a midsection 506, which may also be similarly shaped and configured as the midsection 30 of spacer body 500, as well as an inferior section 508 and superior section 504. The inferior section 508 may include a groove (not shown) for receiving a tongue 510 extending from the inferior section 32 of the spacer body 500. The inferior section 508 may further include grooves 516 for latching to a notch 514 provided on the tongue 510. Legs 402 may extend from the inferior section 508 for hooking onto the median crest of the sacrum 8. The superior section 504 may include a wedge 518 that rests against the outer surface of the superior section of the spacer body 500. A ramp 520 may be provided on the spacer body 500 to limit the extension of the wedge 518 through the brackets 36.

Figure 39:
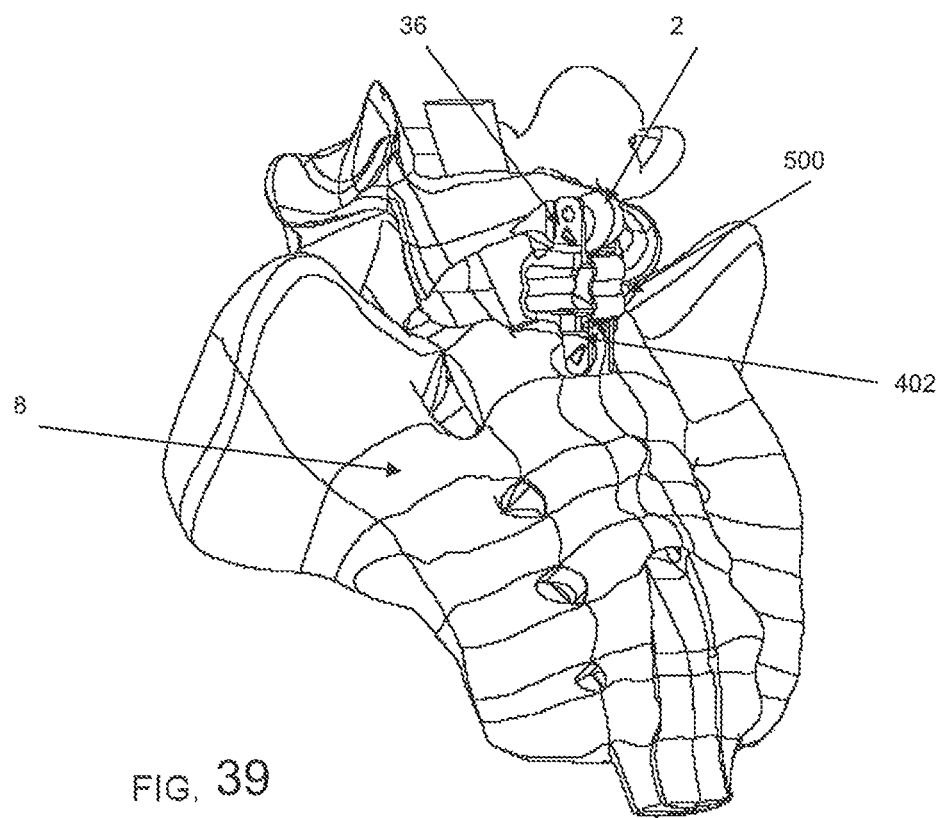
FIG. 39 provides a perspective view of the spacer body of FIGS. 38A and 38B implanted in a patient.

In use, the spacer body 500 may be first inserted by placing the backplate 410 around the sacrum, and positioning the spinous process 2 of the L5 vertebra in between the lateral walls or brackets 36. Next, the side cap or panel 502 may be placed against the spacer body 500 such that the wedge 518 extends under the spinous process and the tongue 510 of the spacer body ratchets into the groove of the cap 502. The legs 402 of the cap may be hooked onto the median crest of the sacrum 8, as shown in FIG. 39.

FIGS. 40A and 40B show another exemplary embodiment in which the spacer body 550 can comprise a two-component assembly. The first component or top portion 552 may include a midsection 30, a superior 34 section, and lateral walls or brackets 36 similar to spacer bodies previously described and shown. As previously discussed, the midsection 30 may have varying thickness or dimensions along its length to provide varying physical properties, or may be shaped or curved as shown, in order to better adapt to the anatomical features of the patient. The lateral walls or brackets 36 may include an aperture 60 for receiving a fastener such as, for example, a rivet. Further, the spacer body 550 may also include surface alterations such as barbs or teeth 40, 512 to facilitate tissue attachment, bonding or fixation. The midsection 30 may extend into an inferior platform 580 having a dovetail projection 582 and a groove 584 thereon, as shown in FIG. 40A. The second component or bottom portion 554 may include a superior platform 570 having a groove 572 thereon and a notch 574 inside the groove 572 to form a dovetail connection with the inferior platform 580 when the first and second components are assembled, as shown in FIG. 40B. A backplate 410 and legs 402 similar to those previously shown and described may be provided on the second component 554.

Figure 41:
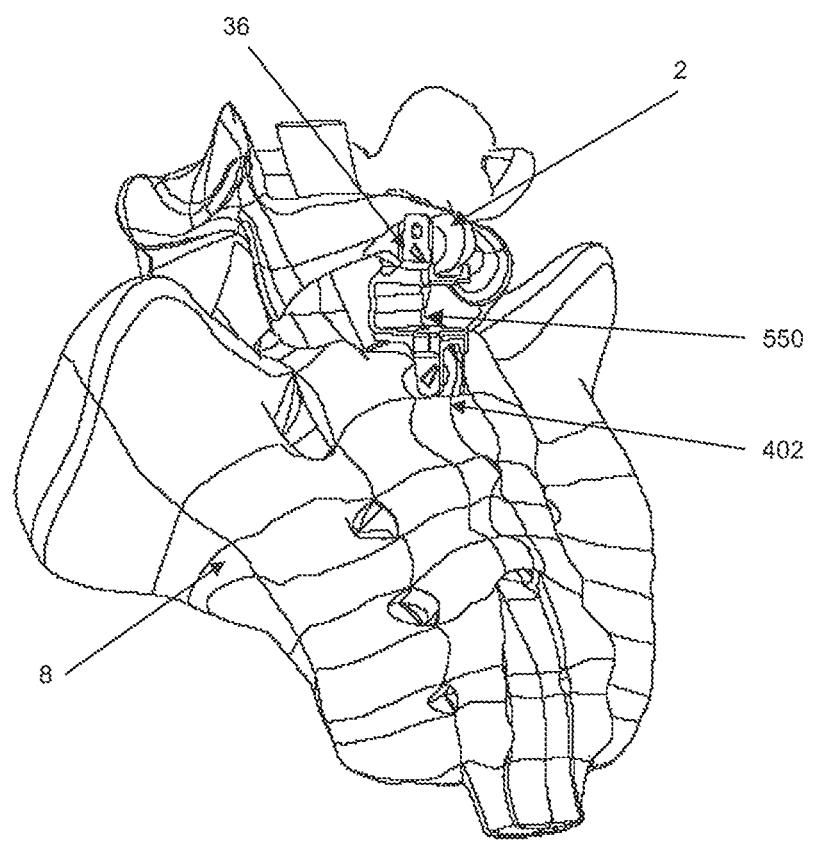
FIG. 41 provides a perspective view of the spacer body of FIGS. 40A and 40B implanted in a patient.

In use, the second component 554 may be placed onto the sacrum 8, with the backplate 410 resting within the sacral canal and the legs extending around the median crest of the sacrum 8, as shown in FIG. 41. Next, the first component 552 may be secured onto the second component 554 by sliding the dovetail projection 582 into the groove 570 of the first component 552, and allowing the groove 584 to catch the notch 574. The spinous process 2 of the L5 vertebra may be positioned within the lateral walls or brackets 36.

It is contemplated that the surgeon may use the devices of the present disclosure to treat a number of clinical problems. For example, the devices may be used to treat degenerative disc disease and/or disc herniation. The devices may also be used to treat spinal stenosis, including central and/or lateral canal stenosis. The devices may be used before, after, or in conjunction with other treatments or implants, including adjacent rigid fixation, adjacent spinal decompression, fusion, and/or facet replacement or repair.

The devices of the present disclosure may be surgically implanted in a variety of ways without impairing the effectiveness of the devices. For example, the surgeon may select a number of different operative approaches and/or incision positions and/or sizes. Further, the surgeon may implant each of the components of the devices in various sequences. The specific operative procedures may be selected based on patient-specific clinical factors.

A number of different incisions and/or operative procedures may be used to implant the devices of the present disclosure. For example, in one embodiment, the surgeon may use a mid-line incision over the lumbar and sacral vertebrae to expose the L5-S1 interspinous region. Alternatively, the surgeon may use one or more incisions positioned lateral to the spine. Further, the surgeon may use a minimally-invasive procedure including various scopes, cannula, and/or robotic implantation devices to deliver the devices to the surgical site.

After making appropriate incisions to expose the operative region, the components of the devices may be implanted using several different steps which may be performed in a number of different sequences. For example, the surgeon may first implant one or more anchors 18 to the sacrum and then implant spacer body 12 in the L5-S1 interspinous space. The spacer body 12 may then be fixed to the fixation rod 16, which may finally be secured to the sacrum 8.

In another technique, the surgeon may first implant the spacer body 12. Anchors 18 may then be secured to the sacrum and the fixation rod 16 may be secured to the anchors 18. The surgeon may complete the procedure by securing the device 10 to the spinous process of the vertebra using one or more ligaments, sutures, and/or rigid fixation caps 220, 260, 280.

Further, the devices may be provided in a partially assembled form. In this embodiment, the spacer body 12 may be pre-assembled and securely fixed to the fixation rod 16. Thus, the spacer body 12 may have a predetermined degree of lateral movement or rotation with respect to the attached fixation rod 16.

In another aspect of the disclosure, the devices may be assembled from a modular kit. The surgeon may individually select the size, shape, and/or physical properties of each component, including the spacer body 12, fixation rod 16, anchors 18, flexible fixation element 180, and/or fixation caps 220, 260, 280. The surgeon may then assemble the components and select an appropriate degree of lateral movement and or rotation for the spacer body 12 and fixation rod 16 as needed.

The anchors 18 may be secured to sacral bone in a variety of orientations. For example, in one embodiment, the device 10 may include two polyaxial screws. The polyaxial screws may be inserted on opposite sides of the sacrum 8. The polyaxial screws may be inserted into the sacral alae or pedicle and may be directed in an anterior-lateral direction. The surgeon may choose a different orientation and anchor placement based on clinical factors such as surrounding bone disease and/or prior surgery or implants.

It is contemplated that the devices 10 of the present disclosure may provide an improved system and method for treating various disorders of the spine. For instance, the devices provide a mechanism for treating disorders of the spine at the L5-S1 vertebral level. Further, the devices of the present disclosure may also be useful for treating diseases of the spine at other vertebral levels. However, the devices of the present invention may also be used to stabilize lumbar vertebrae above the L5 level. For example, in the case of an L5 laminectomy, it is possible to use the present device to stabilize the L4 vertebra while placing the screws of the rod-based device system into the pedicles of the adjacent L5 vertebra, thereby providing a supporting bridge between the L4-L5 region. Accordingly, it is contemplated that the devices provided in this disclosure, and in particular the rod-based systems, may be used to stabilize any pair of adjacent vertebrae by securing the anchors of the rod to the pedicles of the adjacent vertebra to the spinous process being supported.

Furthermore, it is contemplated that the devices of the present invention can be used as an interspinous vertebral stabilization implant for placement between two or more adjacent vertebrae. This can be accomplished by providing devices which have substantially similar features both inferior and superior to the midsection 30 of the spacer body 12. For example, it is possible to provide devices which have brackets 36 similar to those described in FIGS. 10A-14D extending from the superior section 34 as well as the inferior section 32. Similarly, it is contemplated that an implant can be provided which has flanges 206, slots 246, or notches 64 on the inferior section 32 as well as the superior section 34, as illustrated in FIGS. 18A, 19A, and 20A, for use with a fixation cap 220, 240, 260 on both ends of the device.

The methods and devices of the present disclosure may be significantly less invasive and/or produce less drastic and more reversible anatomic changes as compared to other procedures including spinal fusion and total disc replacement. The device of the present disclosure may limit normal spinal motion but provide some controlled movement in flexion, extension, rotation, and/or lateral bending. Further, the devices and methods of the present disclosure may be particularly well-suited for treating various stages of degenerative disc and/or spinal stenosis, particularly at the L5-S1 level.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A lumbosacral interspinous stabilization device, comprising:
    a flexible U-shaped body comprising an inferior section, a superior section, a midsection extending therebetween, and a pair of lateral walls extending from the superior section for engaging a spinous process of a lumbar vertebra, the inferior section including a gripping portion for engagement with a median crest of a sacrum for securing the body between the lumbar vertebra and the sacrum;
    wherein at least one of the lateral walls is secured directly to the superior section of the body by a hinge joint permitting the at least one of the lateral walls to be selectively movable with respect to the other lateral wall.

2. The device of claim 1, wherein each lateral wall contains a through hole for receiving a fixation element.

3. The device of claim 1, wherein the device includes a surface feature for enhanced fixation to bone tissue.

4. The device of claim 3, wherein the surface feature is selected from the group consisting of teeth, barbs, beads, and surface roughening.

5. A lumbosacral interspinous stabilization device, comprising:
    a body comprising an inferior section, a superior section, a midsection extending therebetween, and a pair of lateral walls extending from the superior section for engaging a spinous process of a lumbar vertebra, the inferior section including a gripping portion for engagement with a median crest of a sacrum for securing the body between the lumbar vertebra and the sacrum; and
    a hinge joint permitting at least one of the lateral walls to be movable from a substantially parallel position with respect to the other lateral wall, to a non-parallel position with respect to the other lateral wall.

* * * * *